United States Patent
Olesen et al.

(10) Patent No.: US 8,044,267 B2
(45) Date of Patent: Oct. 25, 2011

(54) RUCOLA PLANTS WITH CYTOPLASMIC MALE STERILITY (CMS)

(75) Inventors: Merete Halkjær Olesen, Ringsted (DK); Henrik Agerskov Romme, Gudbjerg (DK); Hans Henrik Kampmann, Odense S. (DK)

(73) Assignee: Syngenta Participations AG, Basel (CH)

( * ) Notice: Subject to any disclaimer, the term of this patent is extended or adjusted under 35 U.S.C. 154(b) by 794 days.

(21) Appl. No.: 11/854,665

(22) Filed: Sep. 13, 2007

(65) Prior Publication Data
US 2008/0098495 A1 Apr. 24, 2008

Related U.S. Application Data

(60) Provisional application No. 60/845,346, filed on Sep. 18, 2006.

(30) Foreign Application Priority Data

Sep. 13, 2006 (DK) .................................. 2006 01171

(51) Int. Cl.
*A01H 1/02* (2006.01)
*A01H 4/00* (2006.01)
*C12N 15/10* (2006.01)

(52) U.S. Cl. ........ 800/303; 800/269; 800/299; 800/306; 435/6.1; 435/430.1; 435/431

(58) Field of Classification Search .................. None
See application file for complete search history.

(56) References Cited

FOREIGN PATENT DOCUMENTS

| GB | 2 211 205 A | 6/1989 |
|----|-------------|--------|
| WO | WO 92/05251 A | 4/1992 |
| WO | WO 96/21010 A | 7/1996 |

OTHER PUBLICATIONS

Fahleson et al. Theoretical and Applied Genetics 76(4): 507-512 (Oct. 1988).*
Kumar et al. Indian Journal of Agricultural Sciences 56(4): 229-233 (Apr. 1986).*
T. Cardi et al., Theor Appl Genet, 1997, vol. 94, pp. 204-212.
E. Sundberg et al., Theor Appl Genet, 1991, vol. 83, pp. 81-88.
R.C. Yadav et al., National Journal on Plant Improvement, 2002, vol. 1, pp. 42-47.
Agnihotri et al., Plant Breeding, 104, 281-289, 1990.
Fahleson et al., Plant Science, 123, 133-142, 1997.
Matsuzawa et al., Plant Breeding, 118, 82-84, 1999.
Navratilova, Hort. Sci. (Prague), 31, 4, 140-157, 2004.
Sikdar et al., Theor Appl Genet, 79, 561-567, 1990.
S.C. Verma, Incompat. Newsl., vol. 16, p. 9, 1984.
Walters et al., Plant Cell Reports, No. 10, pp. 624-628, 1992.
Hanson et al., The Plant Cell, vol. 16, pp. S154-S169, Supplement 2004.
Wang et al., Euphytica, vol. 151, pp. 111-119, 2006.
Grelon et al., Molecular and General Genetics, vol. 243, pp. 540-547, 1994.
Sigareva et al., Theoretical and Applied Genetics, vol. 94, pp. 213-220, 1997.

* cited by examiner

*Primary Examiner* — David T Fox
(74) *Attorney, Agent, or Firm* — S. Matthew Edwards

(57) ABSTRACT

The present invention discloses rucola plants, including an *E. sativa* plant, with cytoplasmic inherited male sterility (CMS) for hybrid breeding purposes. The present invention includes plants that comprise CMS-cytoplasm from cauliflower (*B. oleracea* var. *botrytis*) transferred to *E. sativa* by a wide interspecific cross.

4 Claims, 16 Drawing Sheets

Figure 10

```
1
ccatgacaataatcttagtcggagtcggagtcaaattccttacctttccacccaaagctgaacatgaacatatccgcacagatattccatttttttattgaggatccatttcgaac
tgaactactcatgctaggcaaacaagcaaggagttgttaataagaggagctacagtgctgcggagttccgtgctgcttattaaggagccggcggcagctacgcaa
cacttcctgcaactcatacctactaacaaactgttactcttttaagagtttagctgcattcctgcgggagttacgtacgcaatcaaagacgcaggcacgttcg
caacacctgcttcaacttcatgcacattagcaacaagattggtagttgattgttggaggatagctgcagctccctacgggagtgaactacagttccaggggagc
acagcaaggccaatacccggctgtgaggcgcgtagccagttgaaagcaatcgagagaaaaccgcccaaatacgcttcgccacgtgtagccctgtatggactcgcgaagcaggt
ataatacgtatataagaagatttcattccagttgatctaactattgagtgaggactacttaccgattgataataccgtataagagaagctgctttgtggagtgatcttct
ctccgtcggtgtccaagatttgaaacgcgctatgtcagattctgcagatttctggggctatgttcagattctgaaccaaagcactgaggttctgaagcctatatgagcagaagtaataaatacctcggggagaagcggg
cgaaatgaattaagtaaggcgctatgttcagattctgcagatttctggggctatgttcagattctgaaccaaagcactgaggttctgaaagcctatatgagcagaagtaataaatacctcggggagaagcggg
tagaggaattggtcaactcatcag
                                                    937nt Oligo 37 →
gctcatgacctgaagattacaggttcaaatcctgtccccgcaccgtagttcattctgcatcactctcctgtcgttatcgacctcgcaagtttttgaaacggccg
aacgggaagtgacaataccgcttttctttcagcatacataaatgcatattcgaaaaattgtccactttgttctaacaacattgtttacgaaccatgagacatctaga
gttagtgtaataagtttctttcttttagctttcttacctaatgccccatatttgctaagctgttttctaacaataaaatcaaatgtacctacgatgaagtgacgaaaaagtctcacctatca
gaagttaaaaattccatatgaatttcagtatgggtgctaggtgtcaaaggggaaataaagaggggaaaatagagaggggaaagaggaa
ttaaaggggaaaatagagggaaaatggaccgagaaaatgctttgtgaaccaattgctttgaccaaaataaagaagaagcaaaatctcattcaattgaaatagaaga
aaaaagaggtgaaaatggaccgagaaaatg
     ← Oligo 38 1449nt
gatctctatgcccctgttcttggtttctcccatgcttttgttgtcaacaaccaacaacttctatagtgtcctcactactcttctactcctagaggcttgacggagtgaa
gctgtctggaggggaatcattgttgtgaaatctaatcatcgctcaactggataaattcactatttcttcacaattcttctgttatgcctttttcttttt
actttctatatttctttcttttagcttttcatgatggagtgtacttgggatcagcagaattctaaaactacgaaccaactgcttcacaccggggaagaccatccagag
caaggacccaacagtttggaagatctctttgagaagaaaatcacttgatctcttgttctggagagtatatgtcagtttattgaagaacatatttattatatcgaagtcctct
acttattgggaaaagaggaggaaaatactgaaggtgatcacttgtaggaattgtaggaagtgttgtacatgggaggatactgccttgccgttcggttcgcggttgactc
cctcaaatatctggtaggtaagactctactgtcttattgaaagttccacctgattgatgcccatcgcgagtgactaagatcggggctaagatcggggcttaagatcggggaactt
agatacctctggtaggtaaagcactctactgtcttattgaaagttccacctgattgatgcccatcgcgagtgactaagatcggggcttaagatcggggaactt
attattttccggtcctctcacaccctttagagctgttttatgaagctgattgtgatggtgatggaggatcc 2427
cgtctcttgacacaaacgttttatgaaggctgattgtgatggtgatggaggatcc 2427
```

RUCOLA PLANTS WITH CYTOPLASMIC MALE STERILITY (CMS)

CROSS-REFERENCE TO RELATED APPLICATIONS

This application claims priority to U.S. Application No. 60/845,346 filed Sep. 18, 2006.

BACKGROUND OF THE INVENTION

Rucola is a traditional salad vegetable originating from the Mediterranean area, which has in recent years also become very popular with consumers in the USA and the EU. Rucola is grown and sold as leaves and is also called rocket, roquette, arugula and others. Rucola includes *Eruca sativa* and a number of species of the genus *Diplotaxis*. *E. sativa* ("cultivated rucola") is faster growing and more cold tolerant than *Diplotaxis* species ("wild rucola") and its taste is milder and therefore preferable in some market segments, whereas *Diplotaxis* species with their stronger taste and longer shelf life are preferable in other market segments. *E. sativa* and *Diplotaxis* are both a member of the Cruciferae family.

Plant breeders have worked to improve the genetic composition of *E. sativa* plants with a view to creating varieties that are superior to known varieties. Examples of desired improvements are plants having increased yields, disease resistance, shelf life, taste, stress tolerance or earliness.

One approach to achieve this goal in vegetable crops has involved crossing desirable genetic traits into plants and then developing them into pure breeding lines by successive generations of self pollination. Superior lines are then combined to form a uniform F1 hybrid that contains the desirable genetic traits and eliminates inbreeding depression. In the vegetable seed markets all major vegetable crops, except lettuce, are today dominated by such superior F1 hybrids due to their clear advantages over non-hybrids.

There is however no cost effective hybridization system available for rucola. This greatly restricts the potential to improve rucola, in particular *E. sativa* plants. There is therefore an unmet need for developments allowing the routine and cost-effective production of hybrids in rucola, in particular in *E. sativa*.

SUMMARY OF THE INVENTION

The instant invention addresses the unmet need for developments allowing the routine and cost-effective production of hybrid plants in rucola, in particular in *E. sativa*. To meet this need the present application discloses male sterile rucola plants, in particular cytoplasmic male sterile (CMS) plants of *E. sativa*. The present application also discloses seeds and part of these plants, and methods of producing such plants.

Rucola plants and in particular *E. sativa* plants characterised by CMS have never been identified and hence it has not been possible to exploit the opportunities given by male sterility in breeding programs in *E. sativa*. However, the present invention provides male sterile *E. sativa* plants produced by transferring a male sterility trait from another species into *E. sativa* through a wide interspecific cross and have surprisingly obtained *E. sativa* plants with commercially acceptable growth and morphological characteristics. In one aspect, the flowers of a plant of the invention have normal *E. sativa* morphology. In another aspect, seed set of a plant of the invention is in the normal range (where the number of seeds/silique is greater than 5, 8, 10, 12, 14, 16, 17, 18, 19 or 20; or between 15-35 on average). In another aspect, the plant morphology of a plant of the invention is identical to *E. sativa* (FIGS. 8 and 9)

The introgression of the CMS trait from another species enables hybrid breeding in this crop and facilitates therefore efficient crop improvement in order to meet emerging market needs such as enhanced yield and disease resistance, and longer shelf life. This benefits all breeders, producers, shippers, traders and consumers of rucola products.

Accordingly the present invention, in one embodiment, provides a male sterile Rucola plant, including a plant that is *Eruca sativa*.

In a further embodiment said plant comprises a male sterile cytoplasm conferring male sterility upon said plant. Accordingly said plant may comprise male sterile cytoplasm from *Brassica oleracea* or *Brassica napus*. For example the male sterile cytoplasm may be transferred from a male sterile cytoplasm donor selected from the group consisting of cauliflower (var. *botrytis*), Brussel sprouts (var. *gemmifera*), white cabbage (var. *capitata*), oxheart cabbage (var. *capitata*), red cabbage (var. *capitata*), savoy cabbage (var. *sabauda*), turnip cabbage (convar. *acephala DC* var. *sabellica*), portugese cabbage (var. *tronchuda*), curly kale cabbage (var. *sabellica*), kohlrabi (var. *gongylodes*), broccoli (var. *italica*), chinese kale (var. *albiflora*), burma sarson (var. *chinensis*), kitchen kale (var. *fimbriata*), thousand-head kale (var. *fruticosa*), collards (var. *sabellica*) and rape seed/canola (*B. napus*).

In a further embodiment said male sterile cytoplasm is an "Ogura" male sterile cytoplasm and the male sterile *Eruca sativa* plant may comprise an orf138 DNA marker. A suitable source of said male sterile cytoplasm is from cauliflower F1 hybrid "Cheddar".

In one embodiment the male sterile *Eruca sativa* plant is RQ5000/06 [NCIMB no. 41429] or progeny or ancestor of said line RQ5000/06 comprising said male sterile cytoplasm.

The *Eruca sativa* plant of the invention may be an inbred or a hybrid.

The invention includes any part of the plant including fruit, seed, pollen, ovule, embryo, leaf, stem, root or any combination thereof.

The invention further provides for use of an "Ogura" male sterile cytoplasm donor to produce a male sterile *Eruca sativa* plant, including for example a donor that is cauliflower F1 hybrid "Cheddar".

The invention further provides a method of producing a male sterile *Eruca sativa* plant comprising the steps of:
a) crossing a cytoplasmic male sterile *Brassica oleracea* or a cytoplasmic male sterile *Brassica napus* plant with an *Eruca sativa* plant,
b) rescuing one or more embryos resulting from the cross of step a),
c) regenerating a plant from one or more embryos of step b) and selecting one or more plant having *Eruca sativa* phenotype,
d) doubling the chromosome number of the plant of step c), and
e) back-crossing one or more plant resulting from step d) with an *Eruca sativa* plant and selecting for one or plant with *Eruca sativa* phenotype.

In one embodiment this method further includes testing for an orf138 DNA marker during selecting one or plant, wherein said selected plant comprises said marker.

A further aspect, the invention provides a method of producing a male sterile *Eruca sativa* plant comprising the steps of:

a. fusing a protoplast from a plant selected from cytoplasmic male sterile *Brassica oleracea*, cytoplasmic male sterile *Brassice napus* and cytoplasmic male sterile *Eruca sativa* plant, with a protoplast from an *Eruca sativa* plant to produce an allogenic cell,
b. regenerating the obtained allogenic cell into a cytoplasmic male sterile *E. sativa* plant having cytoplasmic male sterile cytoplasm
c. pollinating the regenerated plant with pollen from an *Eruca sativa* plant and selecting one or more cytoplasmic male sterile plant progeny.

In one embodiment, this method includes testing for an orf138 DNA marker when selecting the progeny, whereby said selected one or more plant progeny comprises said marker.

A CMS *Eruca sativa* plant obtainable by any of the above disclosed method is also encompassed by the present invention.

In a further embodiment the invention provides a method for transferring male sterile cytoplasm to a male fertile *Eruca sativa* plant comprising the steps of:

a) crossing a cytoplasmic male sterile *Eruca sativa* plant with a male fertile *Eruca sativa* plant,
b) harvesting one or more seed produced by the cross of step a),
c) back-crossing a plant grown from one or more seed of step b) with said male sterile *Eruca sativa* plant and harvesting seed produced by the cross,
d) back-crossing a plant grown from one or more harvested seed of step c) or seed from subsequent back-crossing step with said male sterile *Eruca sativa* plant for one or more back-cross generation until one or more nuclear genes from the male fertile *E. sativa* are transferred to one or more male sterile backcross plant progeny.

According to one embodiment of this method the cytoplasmic male sterile *Eruca sativa* plant is RQ5000/06 [NCIMB no. 41429] or progeny thereof.

The invention further provides a method of producing a leaf of a rucola plant comprising:

a) growing a CMS rucola plant according to the invention until a leaf is produced; and
b) harvesting said leaf.

Additionally the invention provides a method of vegetatively propagating a rucola plant comprising:

a) collecting a tissue of a CMS rucola plant of the invention;
b) cultivating said tissue to obtain proliferated shoots;
c) rooting said proliferated shoots to obtain rooted plantlets.

Additionally the invention provides a method of producing seed of a rucola plant comprising:

a) growing a first CMs rucola plant according to the invention;
b) pollinating said rucola plant with pollen of a second rucola plant; and
c) harvesting seeds from said first rucola plant.

BRIEF DESCRIPTION OF THE FIGURES

FIGS. 5A-5F. CMS marker detection in CMS-*E. sativa* and parent lines. PCR products from amplification of plant DNA extracts using primer combination oligo 37+oligo 38, are analysed on ethidium bromide-stained agarose gels. The 512 bp fragment indicates the presence of "Ogura" CMS and the 630 bp fragment is a positive control for the presence of the cob gene and a positive control for the PCR reaction. PCR products from DNA extracted from plant samples are shown as follows: A: Lanes 1, 4b and 5 are from samples of "Ogura" CMS cauliflowers; lanes 2 and 3b are cauliflowers lacking "Ogura" CMS; lanes 6, 7 and 8b are normal male-fertile *E. sativa* cultivars; lanes 9-16 are different allodiploid CMS-*E. sativa* plants, and lane 4b is cv. "Cheddar" the CMS donor used to generate the CMS-*E. sativa* plants in lanes 9-16. Lane M comprises DNA size markers.

FIG. 10. Nucleotide sequence of "orf138". Nucleotide sequence (2427 nt) of "orf138" gene corresponding to Brassica sp. cybrid mitochondrial DNA ORF158, ORF138 and tRNA-fMet: ACCESSION Z12626. PCR detection of "orf138" DNA marker employs an upper primer (Oligo 37) and lower primer (oligo 38) which amplify a DNA sequence corresponding to nucleotides 937 to 1449 of the shown sequence (highlighted in grey). The annealing position of the primers in the nucleotide sequence is indicated by underlining. PCR amplification with oligo 37 and 38 yields a 512 bp DNA product.

DETAILED DESCRIPTION OF THE INVENTION

Definitions

Figure 1:
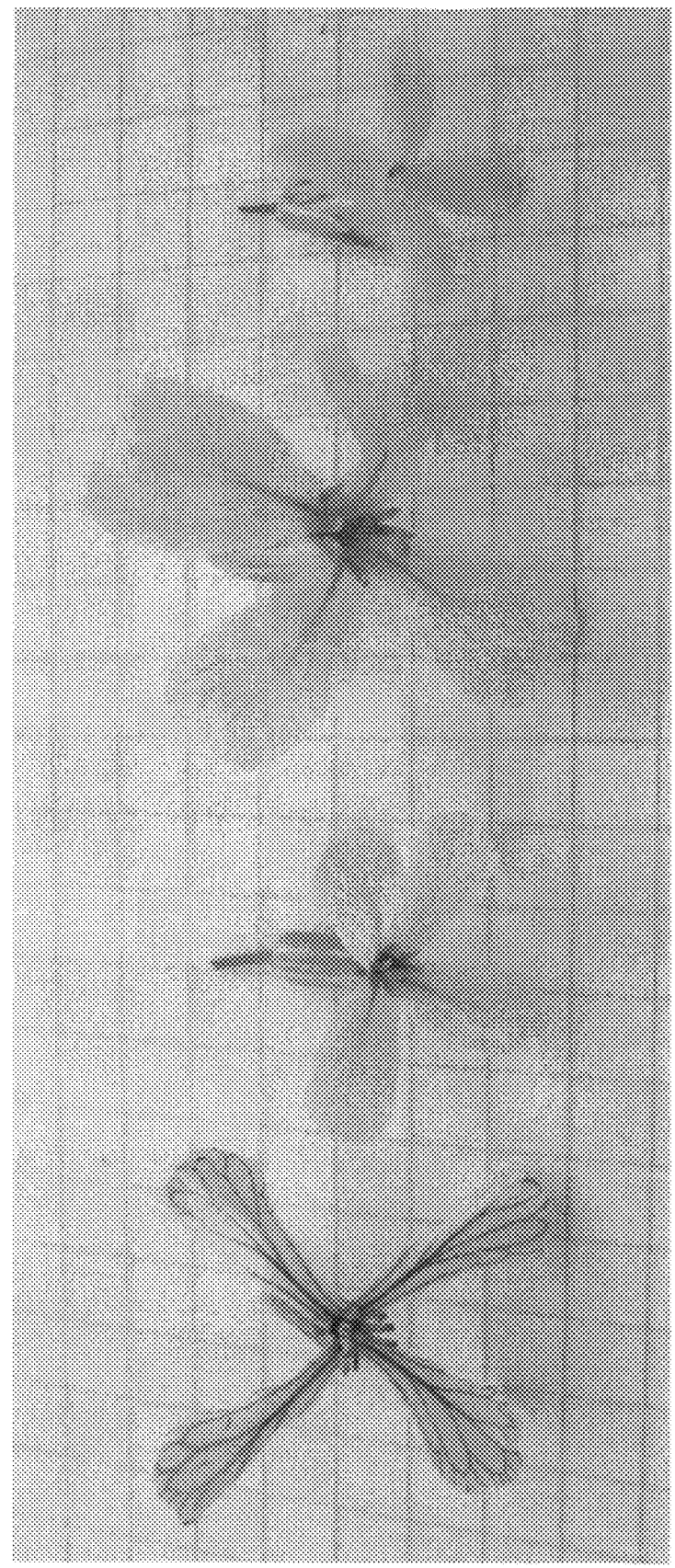
FIG. 1. Comparison of flower morphology. Left: *E. sativa* cv. "Myway"; Center-left: RQ1400/04-1 (CMS cauliflower *B. oleracea* var. *botrytis*×*E. sativa*) F1; Center right: RQ1400/04-1, after chromosome doubling=allotetraploid; Right: CMS cauliflower *B. oleracea* var. *botrytis*. Flowers of RQ1400/04-1 and its allotetraploid derivative (center left+right) have disfunctional anthers, which fail to produce viable pollen.

Agglutination: The formation of clumps of cells.
Allogenic: Genetically different.
Alloplasmic: Organism containing cytoplasm (including mitochondria and chloroplasts) from one species and nucleus from another.
Allotetraploid: Tetraploid produced from a hybrid between two or more different species and therefore possessing two or more different sets of chromosomes.

Amphidiploid: Diploid produced from a hybrid between two different species and therefore possessing two different sets of chromosomes.

BC: Back Cross. Classical breeding technique that can be used to introduce the cytoplasm (or genes) from a donor into a homologous genetic background called the recurrent parent (RP). The female donor is crossed once with the RP, hereby a F1 hybrid is created. The F1 hybrid is then crossed with the RP giving the $BC_1$ generation. $BC_1$ is crossed with RP etc. This is repeated several times. Thereby the homologous genetic line is recreated within the cytoplasm from the donor.

Callus: Mass of undifferentiated cells that initially arises from plant cell or tissue in artificial culture.

CMS: A form of male sterility in plants determined by cytoplasmic factors, usually mitochondrial DNA.

CMS cytoplasm: Cytoplasm containing male sterility determining factors.

Cytoplasm: All the living part of a cell inside the cell membrane and excluding the nucleus.

Cytoplasmic locus "orf138": A specific marker (from INRA) for the "Ogura" male sterility. The primer combination amplifying this marker have the sequences:

```
Oligo37: GCA TCA CTC TCC CTG TCG TTA TCG

Oligo38: ATT ATT TTC TCG GTC CAT TTT CCA
```

The expected amplification product is 512 bp. The sequence of the orf138 gene is available on the public databases (NCBI) at accession N°Z12626.

Endonuclease: Nuclease enzyme that splits DNA at internal sites. By using such enzymes on DNA, a certain unique digestion pattern is obtained. This pattern can be used to distinguish genetically different organisms.

*Eruca sativa* phenotype: is a phenotype characterised by a range of features that distinguish the morphological growth habit of *Eruca stativa* plants, including leaf shape and size, frequency of stem branching, plant height and volume, flower shape and size as illustrated in the figures. Selection of a plant with *Eruca sativa* phenotype can thus include the selection of a plant comprising one or more of these distinguishing morphological features.

F1 hybrid: Seeds or plants originating from a cross between two inbred parent lines. F1 denotes $1^{st}$ filial generation.

Feeder cells: Cells used in e.g. protoplast culture in order to support the development of the fragile protoplasts.

Gamete: Haploid reproductive cell produced by sexually reproducing organisms, which fuses with another gamete of opposite sex or mating type to produce a zygote.

Flow cytometry: Technique for counting cells and distinguishing different types of cells in a mixed population. The cells are usually stained with different flourecent antibodies to distinctive cell surface molecules and a stream of labeled cells is then run through a fluorescence detector, which counts the cells of each type. The method can also be used for determining the amount of DNA in the cells and thereby give an indication of the ploidy level.

Heterokaryon: A cell containing two (or more) genetically different nucei, formed naturally or artificially in culture by the fusion of two animal cells or plant protoplasts.

Inbred: line produced by successive self pollinations.

Interspecific hybrids: Hybrid made from a cross between two different species.

Introgressing: Gradual transfer of a gene from one line to another e.g. by back crossing.

Maintainer plant line: Male fertile plant line used as pollinator for seed multiplication of a specific CMS line. The cytoplasm of the maintainer line is male fertile, but the nuclear chromosomes are identical to the nuclear chromosomes of the specific CMS line.

Male fertile: Organism or plant able to produce viable male gametes.

Male sterile: Organism or plant unable to produce viable male gametes. Partly male sterile means that the amount of viable pollen is insignificant with respect to potential for commercial hybrid seed production from a given female line.

Meiotic pairing: Stage in the meiosis (the process producing gametes), where the homologous chromosomes are aligned on the equator of the cell with all the centromers lying along the spindle equator.

MES: 2-(N-Morpholino) ethanesulfonic acid.

Micro calli: Very small pieces of callus.

Micro-manipulation: Common technique used to handle and sort single cells.

Microsatellite marker: See SSR marker

Mitochondria: Organelles in the cytoplasm of eukaryotic cells, having a double membrane, the inner invaginated, and which are the site of the tricarboxylic cycle and oxidative phosphorylation of oxidative respiration, generating ATP. They contain a small circular DNA which specifies tRNA's, rRNA's and some mitochondrial proteins.

n: Haploid chromosome number.

Nucleus: A large dense organelle bounded by a double membrane, present in eukaryotic cells, and which contains the chromatin and in which the DNA replication and transcription takes place.

NCIMB: National Collection of Industrial Bacteria. The collection also accepts seeds.

Ogura CMS: The term Ogura CMS cytoplasm as used herein refers to *Raphanus sativus* originating cytoplasm comprising mitochondrial DNA which confers male sterility to plants. The term Ogura CMS *Brassica oleracea* plant or plant cell as used herein refers to a *Brassica oleracea* plant or plant cell comprising Ogura CMS cytoplasm.

Osmolarity: The osmotic concentration of a solution.

Osmoticum: Compound used to increase the osmotic concentration of a solution

Ovule: In seed plants, the structure consisting of the megagametophyte and megaspore, surrounded by the nucellus and enclosed in an integument, and which develops into a seed after fertilization.

PCR: Polymerase Chain Reaction. Common technique used to amplify specific regions or fragments of DNA.

Primer: Short specific DNA fragment, in the PCR, a pair of synthetic oligonucleotides (primers) complementary to flanking regions of the DNA to be copied, which are bound to the DNA before the reaction commences to ensure that DNA replication is initiated at the required points.

Ploidy-level: Number of chromosomes or DNA molecules in a cell or organelle, or the typical chromosome number of a multicellular organism.

Protoplast: plant cell with cell wall removed; the living component of a cell, i.e. the protoplasm not including any cell wall.

SSR marker: Simple Sequence Repeat. Certain areas of the genome containing repeated simple sequences e.g. ATT n times. These repeats are known to have a high degree of polymorphism and are therefore useful as DNA markers.

Triploid: An organism with three sets of chromosomes per somatic cell.

Exploiting hybrid opportunities in rucola would significantly increase the efficiency of rucola breeding, since inbreeding depression of a number of traits could then be eliminated.

One method of producing hybrids relies on male sterility in the breeding line for which hybridization is desired. Male sterile lines allow the breeder to produce hybrid seed by controlling cross-fertilization in the flowers of the breeding line (i.e. mother line). Cross-fertilization is secured and self-fertilization eliminated by using breeding line plants that are male sterile due to their failure to produce viable pollen. 100% hybridization of the male sterile breeding line with the desired father line can then be obtained.

Several sources of CMS can be used in the context of the present invention, for example: "Ogura" male sterile cytoplasm of *Raphanus sativus*); "Polima" male sterile cytoplasm of *B. napus*, and "Nap" male sterile cytoplasm of *B. napus* and "Anand" male sterile cytoplasm of *Brassica toumefortii* (Cardi, T. & E. D. Earle, 1997).

Plants carrying CMS can become male fertile again, or partly male fertile, in the presence of certain nuclear genes. These nuclear genes are called "restorer genes" because they counteract the effect of the CMS cytoplasm. Male fertility can be restored in the F1 hybrid by crossing with a pollinator line carrying restorer genes.

Crosses between different species of Cruciferae would facilitate the transfer of desirable genes, such as cytoplasmic male sterility, between species. However, the production of interspecific hybrids is generally unpredictable and often extremely difficult to accomplish due to the need to overcome the natural genetic barriers that exist between species.

Another way of producing interspecific hybrids, comprising cytoplasmic genes from one species and nuclear genes from another, is by protoplast fusion. Here a protoplast from a species having desirable traits is combined with a protoplast from a CMS plant from another species. The nuclear material of the CMS donor is removed, or inactivated, prior to fusion, so it donates only the cytoplasm. The resulting cytoplasmic hybrid or "cybrid" is then re-generated into a plant. This plant will possess the nuclear genes for the desirable traits and be male sterile. This procedure is as unpredictable for the generation of interspecific hybrids as the crossing method outlined above.

The barrier for obtaining a true interspecific hybrid can either be caused by the inability of the foreign pollen tubes to penetrate into the ovarian tissue of the pollen acceptor, or be caused by elimination of all the chromosomes of one of the parents, typically the father. In a cross between *E. sativa* and *B. oleracea*, Yadav et al. 2002 showed that *E. sativa* did not function as a pollen acceptor. In the reciprocal cross, limited fertilization occurred, and only few pollen tubes were seen in the ovarian tissue of *B. oleracea* after 24 h of pollination. Sundberg & Glimelius, 1991 showed that in a cross between *B. napus* and *E. sativa*, the chromosomes of the *E. sativa* genome appeared to be preferentially sorted out. A similar mechanism was observed in the initial *B. oleracea*×*E. sativa* crosses made for this invention, in which only a few plants, derived from embryo-rescued seeds, phenotypically resembled true interspecific hybrids between *E. sativa* and *B. oleracea*. The rest of the plants were phenotypically similar the *B. oleracea* female line. The production of CMS rucola plants (e.g. CMS *E. sativa*) according to the present invention has thus surprisingly been achieved as detailed below.

Seeds of line RQ5000/06, a representative plant according to the present invention, have been deposited with NCIMB ltd., Buckburn, Aberdeen, AB21 9YA, on Aug. 14, 2006 under accession number NCIMB 41429.

I. Crossing Program for Production of CMS *E. sativa*

The present invention discloses rucola plants (e.g. *E. sativa* plants) with CMS, introgressed from *B. oleracea*. *E. sativa*, itself, cannot be used as a CMS donor to obtain a CMS rucola hybrid, because the CMS trait has never been reported in these plants.

Interspecific hybridization is performed by crossing a CMS donor as mother such as cauliflower (var. *botrytis*), Brussel sprouts (var. *gemmifera*), white cabbage (var. *capitata*), oxheart cabbage (var. *capitata*), red cabbage (var. *capitata*), savoy cabbage (var. *sabauda*), turnip cabbage (convar. *acephala DC* var. *sabellica*), portugese cabbage (var. *tronchuda*), curly kale cabbage (var. *sabellica*), kohlrabi (var. *gongylodes*), broccoli (var. *italica*), chinese kale (var. *albiflora*), burma sarson (var. *chinensis*), kitchen kale (var. *fimbriata*), thousand-head kale (var. *fruticosa*), collards (var. *sabellica*) and from rape seed/canola (*B. napus*), and *E. sativa* as father. When CMS is introgressed from a cauliflower (*B. oleracea* var. *botrytis*) donor, it provides favourable flower morphology. Since cauliflower (n=9) has a diploid genome of 18 chromosomes, and *E. sativa* (n=11) has a diploid genome of 22 chromosomes, they are not sexually compatible. In the developing seed this incompatibility can result in incomplete degradation of the endosperm needed to support embryo maturation, and the loss of chromosomes from the pollinator. The growth and survival of embryos produced by the cross may however be secured by employing the "embryo rescue" technique.

Embryo rescue involves removing the embryo from the silique produced by the cross, about 3 weeks after pollination, the exact timing of embryo rescue depending on the time of the year and the parent lines in the cross. The siliques are first treated with a disinfectant and then rinsed in sterile water to eliminate microbial contamination. The siliques are then cut open and the embryos are removed and placed on a suitable medium to facilitate growth, as for example MS (Murashige & Skoog medium) detailed in Table 1. The embryos are then grown at approximately 25° C. in a dark/light regime until they have germinated and developed roots, after which they are transferred to soil and grown under a day/night regime of about 20° C. night and 22-25° C. day.

Regenerated F1 plants are grown to maturity, and those producing flowers with dysfunctional anthers lacking pollen are expected to carry the CMS trait. F1 plants that have both the CMS trait and exhibit desired traits conferred by the paternal parent may be identified by their phenotypic properties. Growth properties and morphology that may be selected for include vigorous growth, shelf-life (increased lead thickness and surface wax), flavour (bitterness), disease resistance, dry matter content, low nitrate content). By way of example, a cross between CMS *B. oleracea* and *E. sativa* produced an F1 plant (plant no. RQ1400/04-1), whose growth was more vigorous than a normal rucola, but its volume was smaller than a cauliflower. The leaves were serrated like the parental type of *E. sativa* during the entire growth. The flowers of the plant clearly carried the CMS trait, producing disfunctional anthers without pollen, but otherwise having a phenotypically normal cruciferous flower type (FIG. 1, second from left) when compared to flowers of the two parental lines of the cross (FIG. 1, left and right). Despite conducting a very large number of crosses between the RQ1400/04-1 plant and *E. sativa* pollinators, throughout the entire flowering period, no seeds or even embryos were obtained.

The chromosome complement of the hybrid F1 plants generated from a cross between a *B. oleracea* CMS donor and an *E. sativa* cv can be determined by extracting nuclei from the hybrid plant material and measuring the amount of DNA by flow cytometry. Different protocols for the isolation of nuclei and preparation of stained nuclei suspensions for flow cytometry can be used, as exemplified in example 1. As shown in Example 1, the DNA content of RQ1400/04-1 was consistent with an amphihaploid plant, having one set of 9 chromosomes from cauliflower and one of 11 from E. sativa (FIG. 4). Such plants can be propagated vegetatively, and the clones maintained in vivo, however they may be found infertile when crossed to other E. sativa pollinators. If the chromosomal complement of a hybrid F1 plant comprises a cauliflower chromosome set and an E. sativa chromosome set, as is the case for RQ1400/04-1, then the plant is likely to be infertile due to an inability to conduct normal meiotic pairing and form fertile gametes as required for subsequent formation of progeny. In this case it is desirable to double the chromosome complement of the hybrid F1 plant to generate a plant with 2 sets of cauliflower chromosomes and 2 sets of E. sativa chromosomes. Such chromosome-doubled plants are capable of undergoing meiosis since the 2 sets of chromosomes can perform chromosomal pairing internally and the plants are thus fertile. A chromosome doubling strategy, employing colchicine treatment, was successfully employed to generate a fertile derivative of vegetative clones of RQ1400104-1 plants (Example 1D).

Seedlings of CMS hybrid F1 plants that have undergone successful chromosome doubling are recognised by their distinctive phenotype, including vigorous growth of stems and leaves, and flowers of up to double their normal size, while retaining their CMS-phenotype with rudimentary anthers devoid of pollen. During the flowering period, these colchicine-treated plants may be back-crossed with E. sativa cultivars to produce viable seed. Progeny plants are selected for the CMS trait and for inheritance of desired E. sativa traits including for example serrated leaf habit, E. sativa flower morphology, vigorous growth, fertility, high seed set, shelf-life (increased lead thickness and surface wax), flavour (bitterness), disease resistance, dry matter content, low nitrate content).

The chromosome complement of a selected hybrid back-cross may be determined by extracting nuclei from a sample of hybrid plant material and flow cytometry. The selected back-crossed progeny ($BC_1$) may, for example, be found to be triploid with a chromosome complement consistent with one set of cauliflower chromosomes (n=9) and 2 sets of E. sativa chromosomes (n=11) giving a total of 31 chromosomes as seen for BC1 lines derived from RQ1400/04-1 plants (Example 1D).

DNA marker analysis, may be employed to demonstrate the presence of the "Ogura" CMS in the $BC_{>1}$ progeny, as illustrated using the "orf138" marker in example 13+FIG. 5.

The selected $BC_1$ generation may have a reduced fertility and may not have all the desired traits from the E. sativa parent, in which case a back-crossing program may be performed between the selected $BC_1$ plant and the desired E. sativa paternal line. As illustrated in Example 1, the back crossing of the triploid $BC_1$ plant RQ1438/05-1 to E. sativa cv. "Myway" generated a number of $BC_2$ plants, whose morphology closely resembled E. sativa as well as retaining male sterility. Flow cytometry analysis indicated that these $BC_2$ plants had reverted to diploid chromosome complement.

Figure 9:
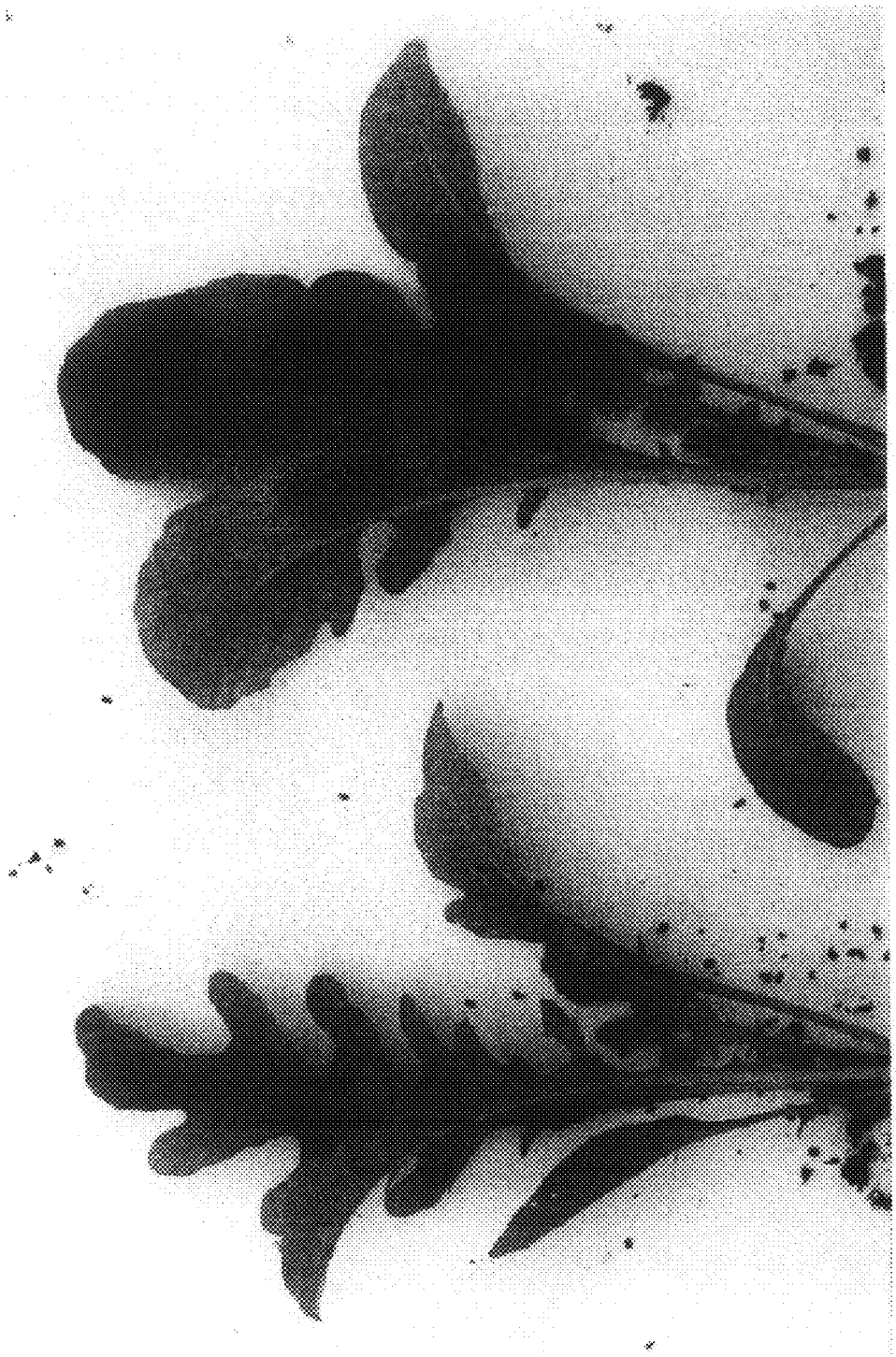
FIG. 9. Comparison of plant morphology. Left: CMS-*E. sativa* $BC_3$ plant. Right: *E. sativa* cv. "Myway". It is seen that the plants are almost identical.

Hence a back-crossing program starting from the selected $BC_1$ plants can generate plant lines that yield similar number of seeds as their recurrent parent E. sativa and produce leaves compatible with commercial leaf production, as illustrated for the $BC_2$ plant RQ1438/05-1 in Example 1 and FIG. 9.

The amount of B. oleracea DNA still present in the $BC_>$, plants generated from back-crossing, may be determined by DNA marker analysis, for example by using 72 SSR markers covering the whole C-genome of B. napus was performed. In Example 14, the CMS $BC_3$ plants were shown to have a very high homology to E. sativa, and that all of the B. oleracea chromosomes had been eliminated in the back-crossing process.

II Protoplast Fusion Program

CMS E. sativa plants can also be prepared by protoplast fusion. The protoplasts can be obtained from a B. oleracea or B. napus plant that contains the "Ogura" CMS cytoplasm and is male sterile and E. sativa plants with desirable agronomic traits. Suitable CMS donor plants include B. oleracea plants e.g. cauliflower cv. "Cheddar" or other CMS B. oleracea or B. napus varieties.

Protoplasts can be obtained from green plant material e.g. leaf material and from white plant material e.g. etiolated seedlings, according to the method described in example 2 (Glimelius (1984), Physiologia Plantarum 61:38). When protoplasts are isolated from white plant material it is advantageous to stain it with a flourescent dye to facilitate selection of the best material, see example 2C. After protoplast isolation the nucleus in the CMS containing protoplast must be inactivated by irradiation.

The inactivation of the nucleus by irradiation can be effected with the aid of gamma, UV or X-rays. Where irradiation is effected with an X-ray source, nucleus inactivation will in general be obtained by applying a dose of e.g. 10 krad. min for 3 to 20 minutes. The appropriate X-ray dosage may for example be established by determining the maximum level of X-ray irradiation killing 100% of the protoplast population: the percentage of dead cells is estimated by counting the number of formed colonies after 10 to 20 days in culture. Based on the optimum level X-ray irradiation required, protoplast fusion is performed with an irradiated CMS protoplast (with inactivated nucleus) and the E. sativa protoplast.

Fusion of isolated protoplasts may then be accomplished by employing polyethylene glycol (PEG) which causes agglutination, in the presence of a high pH fusion buffer, which promotes membrane fusion between protoplasts. Somatic hybridization may be performed under the conditions disclosed by Sundberg et al., (Plant Science, 1986, 43:155), hereby incorporated by reference, for the production of interspecific hybrids or modifications thereof. However, one skilled in the art would recognize that protoplast fusion can be accomplished by means other than using polyethylene glycol (PEG). For example, the protoplasts can be fused by using electric field-induced fusion techniques as described by Koop et al. in Electroporation and Electrofusion in Cell Biology, edited: Neuman et al. pgs 355-365 (1989), herewith incorporated by reference. Additionally, protoplast fusion can be accomplished with dextran and polyvinyl alcohol as described by Hauptmann et al., "Carrot×Tobacco Somatic Cell Hybrids Selected by Amino Acid Analog Resistance Complementation", 6th International Protoplast Symposium, Basel, Aug. 12-16, 1983, herewith incorporated by reference.

If protoplast fusion is to be accomplished with polyethylene glycol, the procedure described below can be used.

The protoplast fusion is conveniently effected in a washing solution (W5'), described below, containing an osmoticum e.g. a carbohydrate such as mannitol, sorbitol, glucose, or sucrose, and potassium and calcium salts. The pH can range from 5.2 to 10 and is preferably about 5.7. The protoplasts of different origin are mixed and concentrated, conveniently to a final density of $1 \times 10^5$ and $1 \times 10^8$ protoplasts per ml.

The protoplast mixture should then be left undisturbed in a container (e.g. petri dish) for at least 10 minutes to allow the protoplasts to settle at the bottom of the container. The mixture is then treated with polyethylene glycol (PEG), preferably having a molecular weight of 1500 to 6000. In general, good results are obtained when employing an aqueous solution (PFS) comprising 18.8% by weight of PEG at a volume ratio of W5' to PFS of 10:1 to 1:1. PFS comprises conveniently an osmoticum and a calcium salt. The protoplasts are incubated in PFS for 15 to 20 minutes depending on the fragility of the cells.

The fusion is accomplished by washing the protoplasts, for example, three times, with washing solution (W5') containing an osmoticum (e.g. glucose) in a concentration having a lower osmolarity than PFS and potassium, sodium and calcium salts. The fusion procedure is carried out at a temperature in the range between 16° C. and 20° C., for example 18° C. The concentration of PEG in the fusion mixture is gradually decreased with each consecutive washing step (see e.g. example 10). Each washing step should take at least 5 minutes to allow the protoplasts to adjust slowly to the lower osmolarity of the medium, and avoid the protoplasts bursting. After the washing steps have been accomplished, the fused protoplasts should be in the range of $1 \times 10^5$ to $1 \times 10^6$ protoplasts per ml.

Hybrids can then be regenerated in the presence of non-fused parental protoplasts or after their isolation from the culture by selection.

Selection of the hybrids from the non-fused protoplasts can be done by staining and seperation by a micromanipulator or by flow cytometry containing a cell sorting function.

If the protoplasts are stained with fluorescein diacetate the protoplast of hypocotyl origin will stain yellow under a UV light and protoplast from leaves containing chloroplast will give a red auto-fluorescens under UV light (Sunderberg and Glemelius. 1986, *Plant Science* 43:155-162; Glimelius et al., 1986, *Plant science* 45:133-141).

The obtained fusion products can be cultivated in an appropriate culture medium comprising a well-balanced nutrient supply for protoplast growth. The medium contains micro- and macro-elements, vitamins, amino acids and small amounts of carbohydrates, e.g. various sugars such as glucose. Glucose serves as a carbon source as well as an osmoticum. The culture medium also comprises plant hormones (auxins and cytokine) which are able to regulate cell division and shoot regeneration. Examples of suitable auxins include naphtyl acetic acid (NAA), 2,4-dichlorophenoxyacetic acid (2,4-D) and indoleacetic acid (IAA). Examples of suitable cytokinins include benzyl aminopyrine (BAP), zeatin (Zea) and gibberellic acid (GA3). In general NAA and 2,4-D are used in combination with BAP to initiate cell division, in which case the ratio of auxin/cytokinin must be high, for example greater than 1. Two or three days after the fusion treatment, the medium is largely replaced by culture medium (BP) which comprises agarose, in which the fusion products and the parental protoplasts are embedded.

After 14 days, the concentration of auxins is diluted by addition of a culture medium containing no or substantially-less auxins. Star-shaped micro calli will generally develop after 3 to 4 weeks. Such micro calli are then transferred to a regeneration medium to initiate shoot formation, preferably after adaption in an intermediate regeneration medium to allow the cells to adjust to differences in the composition and physical properties of the culture medium and the regeneration medium. In order to induce shoot formation, the auxin/cytokinin ratio in the regeneration medium should preferably be low, e.g. below 1:10. In general it will be preferable to employ the auxin NAA in combination with the cytokinins Zea and BAP for shoot regeneration. The nutrient content of the regeneration media, BR and K3, is relatively compared to that of the culture medium, since they contain less vitamins, a lower of carbon source content comprising solely sucrose and xylose, and do not contain amino acids. The regeneration media also have a higher viscosity than the culture medium. The regeneration medium Br is a solid medium and contains the growth regulators 2,4-D, NAA and BAP, with the ratio of auxin to cytokinin being less than 1. Medium K3 contains Zea, GA3 and also silver nitrate to promote the shoot development.

After two weeks regeneration on Br medium, calli of approximately 3 mm in diameter are transferred to K3 regeneration medium containing a low sucrose concentration. At this stage shoots will develop within 2 to 3 weeks. The obtained shoots are then rooted on a basic medium, such as B5, without additional hormones. The nuclear DNA and mitochondrial DNA of the obtained plantlets may then be identified by standard methods known in the art, e.g. employing suitable restriction endonucleases and comparing the thus obtained DNA digestion pattern of DNA from the fusion products with that of the parental lines.

As described above, after the fusion, the hybrid cells are regenerated to form *E. sativa* plants containing the CMS cytoplasm. These plants may be subsequently back-crossed with other *E. sativa* plants.

It will be appreciated that the *E. sativa* plant of this invention may be employed as starting material for the preparation of other *E. sativa* varieties having CMS by in vitro and/or crossing techniques. Such in vitro and crossing techniques are known in the art by the skilled breeder.

EXAMPLE 1

CMS *E. sativa* Generated by a Crossing Program

Interspecific hybridization was carried out using an orange cauliflower F1 hybrid "Cheddar" (Seminis Vegetable Seeds) as mother, and *E. sativa* cv.

"Myway" (L. Dæhnfeldt A/S) as father. Numerous interspecific crosses were performed of which a total of 10 F1 plants were regenerated by employing the following embryo rescue procedure:

A. Embryo Rescue

Approximately 3 weeks after cross-pollination, the siliques were harvested from the pollinated parent plant. The siliques were disinfected for 20 minutes in a 2.5% corsoline solution and rinsed three times in sterile water. The siliques were then cut in a longitudinal direction and the embryos removed and plated on MS medium (Table 1), with 3% sucrose and without hormones, in a plastic container. The embryos were then grown at 25° C. in 16 h light for at least two weeks. When the embryos had germinated into plants and developed roots they were subcultured on peat, covered with white plastic, and grown for 5-7 days in a greenhouse under 20° C. night and 22-25° C. day regime.

TABLE 1

Composition of embryo growth and regeneration media (1 l).

|  | MS | MAC | 8P | Br | K3 | B5 |
|---|---|---|---|---|---|---|
| $CaCL_2 \cdot 2H_2O$ | 440 mg | 600 mg | 600 mg | 300 mg | 300 mg | 150 mg |
| $CoCl_2 \cdot 6H_2O$ | 0.025 mg | 0.025 mg | 0.025 mg | 0.025 mg | 0.025 mg | 0.025 mg |
| $CuSO_4 \cdot 5H_2O$ | 0.025 mg | 0.025 mg | 0.025 mg | 0.025 mg | 0.025 mg | 0.025 mg |

TABLE 1-continued

Composition of embryo growth and regeneration media (1 l).

| | MS | MAC | 8P | Br | K3 | B5 |
|---|---|---|---|---|---|---|
| FeNa EDTA | 40 mg | 40 mg | 40 mg | 40 mg | 40 mg | 40 mg |
| $H_3BO_3$ | 6.20 mg | 3 mg | 3 mg | 3 mg | 3 mg | 3 mg |
| $KH_2PO_4$ | 170 mg | 164 mg | 164 mg | | | |
| KI | 0.83 mg | 0.75 mg | 0.75 mg | 0.75 mg | 0.75 mg | 0.75 mg |
| $KNO_3$ | 1900 mg | 956 mg | 956 mg | 1556 mg | 1556 mg | 3000 mg |
| $MgSO_4 \cdot 7H_2O$ | 370 mg | 300 mg | 300 mg | 250 mg | 250 mg | 250 mg |
| $MnSO_4 \cdot 4H_2O$ | 22.3 mg | 10 mg | 10 mg | 10 mg | 10 mg | 10 mg |
| $Na_2MoO_4 \cdot 2H_2O$ | 0.025 mg | 0.025 mg | 0.025 mg | 0.025 mg | 0.025 mg | 0.025 mg |
| $NH_4NO_3$ | 1650 mg | 600 mg | 600 mg | 250 mg | 250 mg | |
| $ZnSO_4 \cdot 7H_2O$ | 8.6 mg | 2 mg | 2 mg | 2 mg | 2 mg | 2 mg |
| Myo-inositol | 100 mg | | 100 mg | | | |
| Thiamine | 0.10 mg | 10 mg | 10 mg | 10 mg | 10 mg | 10 mg |
| Pyridoxine | 0.5 mg | 1 mg | 1 mg | 1 mg | 1 mg | 1 mg |
| Nicotinic acid | 0.5 mg | 1 mg | 1 mg | 1 mg | 1 mg | 1 mg |
| Glycine | 2 mg | | | | | |
| Sodium Pyruvate Citric Acid Maleic acid | | 20 mg 40 mg | 20 mg 40 mg | | | |
| Fumaric acid | | 40 mg | 40 mg | | | |
| Glucose | | 40 mg | 40 mg | | | |
| Casein | | 250 mg | 250 mg | | | |
| NAA | | 0.1 mg | 0.1 mg | 0.1 mg | | |
| 2,4D | | 0.2 mg | 1 mg | 0.1 mg | | |
| Zeatin | | | | | 0.26 mg | |
| BAP | | 0.5 mg | 0.5 mg | 0.5 mg | | |
| $GA_3$ | | | | | 0.006 mg | |
| $AgNO_3$ | | | | | 5 mg | |
| Xylose | | | | 250 mg | | |
| Sucrose | 30 g | 80 g | 50 g | 40 g | 10 g | 20 g |
| Agar | 8 g | | | | 8 g | 8 g |
| Agarose | | | | 16 g | | |

B. Phenotypic Properties of F1 Hybrid Plants

From the 10 regenerated F1 plants obtained from the interspecific cross, five clearly exhibited a cauliflower phenotype whereas the other five clearly exhibited the serrated leaf phenotype of E. sativa. Only one of these latter plants survived to the sexual stage (plant no. RQ1400/04-1). During the entire growth, the phenotype of this single plant closely resembled a cross between E. sativa and cauliflower. It was more vigorous than a normal rucola, but the volume of the plant was smaller than a cauliflower. The leaves were serrated like the parental type of E. sativa during the entire growth. The flowers of the plant clearly carried the CMS trait, producing disfunctional anthers without pollen, but otherwise having a phenotypically normal cruciferous flower type (FIG. 1, second from left). This plant was propagated vegetatively, and the clones maintained in vivo.

C. DNA Content of Hybrid Plants

In order to determine the chromosome content of hybrid lines produced by the interspecific cross of orange cauliflower F1 hybrid "Cheddar" and E. sativa cv. "Myway", DNA was extracted from leaf material of the plants and analysed by flow cytometry according to the following protocol.

A small piece of the leaf sample (0.5 cm$^2$) was chopped with a sharp scalpel in a petri dish containing 2.5 ml of a detergent buffer (table 2). The suspension of nuclei released from the cut tissue was filtered through a 50 mm nylon mesh to remove large tissue and cellular fragments. After 5 minutes of incubation, 5 ml of a staining solution (table 3) was added to the sample and after 10 minutes of incubation the sample was ready to be analysed by using Flow cytometer (Partec GmbH, Munster, Federal Republic of Germany). The sample of stained nuclei are transferred to sample tube, placed in the sample holder on the Flow cytometer, and the DNA content is measured and plotted in histogram format.

The DNA content of RQ1400/04-1 was consistent with an amphihaploid plant, having one set of 9 chromosomes from cauliflower and one of 11 from E. sativa (FIG. 4 C compared to the DNA content of the parental lines shown in 4 A and B).

TABLE 2

| Detergent solution (100 ml) |
|---|
| 100 ml distilled water |
| 2.1 g citric acid•$H_2O$ |
| 0,5 ml Tween 20 |

TABLE 3

| Staining solution (100 ml) |
|---|
| 100 ml distilled water |
| 7.1 g $Na_2HPO_4 \cdot 2H_2O$ |
| 0.2 mg DAPI (4,6-diamidino-2-phenylindole) |

D. Producing a Fertile Derivative of CMS F1 Hybrid RQ1400/04-1

A very large number of crosses (>1000) between the RQ1400/04-1 plant and E. sativa pollinators were made, throughout the entire flowering period, however no seeds or even embryos were obtained. Infertility was attributed to amphihaploid chromosome complement of the RQ1400/04-1 plant, and the inability to conduct normal meiotic pairing during gametogenesis. The plants were thus treated with colchicine, according to the following protocol, to produce fertile plants with a doubled chromosome complement, capable of undergoing normal meiosis.

Vegetative clones of RQ1400/04-1 plants, comprising 10 cm rooted seedlings, were first washed in water and then dipped in a 0.34% (W/V) solution of colchicine for 3 hours. The seedlings were then rinsed and potted in a sphagnum mix in a ratio of 1000 liter spaghnum (type "Brun Stenrøgel") to 1 kg of CaCO₃ (chalk) [supplied by Stenrøgel A/S, Stenrøgelvej 13, Thorning, 8620 Kjellerup, Denmark].

Figure 2:
FIG. 2. Comparison of plant morphology. Left: $BC_1$ plant (*E. sativa*×*B. oleracea*)×*E. sativa* (No. RQ1438/05-1). Right: *E. sativa* cv. "Myway". It appears that the $BC_1$ has *E. sativa* serrated leaf shape but the plant is more vigorous and leaves are larger than normal *E. sativa*.
Figure 3:
FIG. 3. Comparison of leaf shapes. Left: leaf of *B. oleracea* var. *botrytis* cv. "Cheddar" Centre left: Leaf from $BC_1$ plant RQ 1438/05-1; Centre right: leaf of $BC_2$ plant RQ 5000/06. Right: Leaf of *E. sativa* cv. "Myway". $BC_1$ and $BC_2$ leaves exhibit a shape similar to rucola.
Figure 6:
FIG. 6: Normal fertile and male sterile "Ogura" flower structure. Right: normal *E. sativa* anthers with pollen. Left: Anthers from CMS+*E. sativa* plant without pollen.
Figure 7:
FIG. 7: Magnified image of normal fertile and male sterile "Ogura" anther structure. Left: normal fertile *E. sativa* anther with pollen. Right: CMS-*E. sativa* anther.

On reaching the flowering stage, approximately 50% of the plants had a phenotype characteristic of plants following chromosome doubling, including extraordinary vigorous growth of stems and leaves, and flowers of almost double their normal size (FIG. 1, center right). The flowers of these plants retained their CMS-phenotype with rudimentary anthers devoid of pollen (FIGS. 6 and 7). During the flowering period, these colchicine-treated plants were crossed extensively (>2.000 pollinations) with the *E. sativa* cultivars "Runway" and "Myway". Progeny were obtained from these crosses comprising a total of only 4 seeds from the cv. "Runway" crosses and 4 seeds from the cv. "Myway" crosses. The seeds were harvested but only 1 seed from the cv. "Runway" cross (No. RQ1437/05-1) and 2 seeds from the cv. "Myway" cross (No. RQ1438/05-1 and -2) germinated. These plants were again clearly more vigorous than a normal rucola (FIG. 2). The leaves were serrated like the parental type of *E. sativa* during the entire growth (FIG. 3).

Figure 4A:
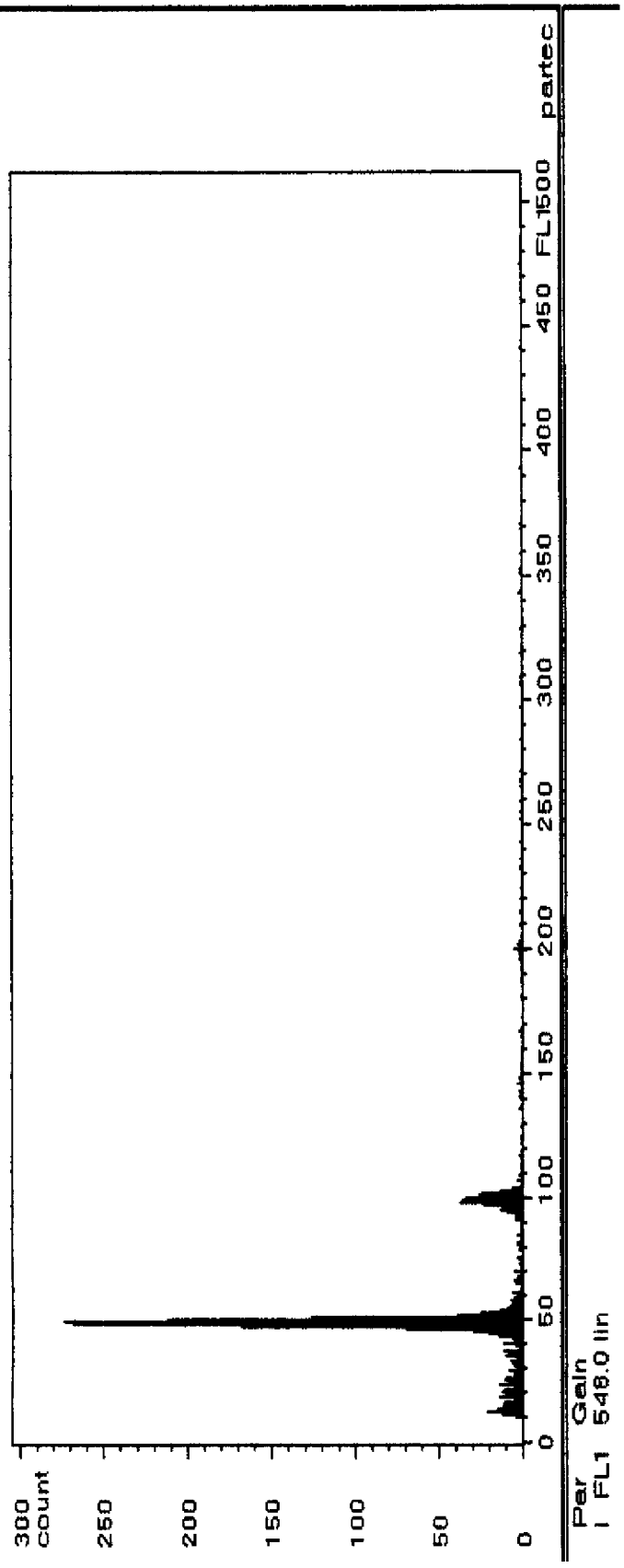
FIGS. 4A-4F. DNA content of plant material measured by flow cytometry. The detectable DNA content of plant material from each of (A) *E. sativa* cv. "Myway"; (B) Cauliflower cv. "Cheddar" and (C) R01400/04-1 corresponds to a value of about 50 FL units, compared to a value of about 75 FL units in plant material from RQ1438/05-1 (D), indicating that RQ1438/05-1 has 3 genomes, i.e. is triploid. (E) $BC_2$ plant RQ 5000/06-3 is diploid, as also observed in plants RQ 5000/06-1, -2 and -4, whereas plant RQ 5000/06-5 (F) appears to have 3 chromosomal sets from *E. sativa* and 1 from *B. oleracea*. X-axis (FL1)=fluorescence intensity units and count=total counts.
Figure 4B:
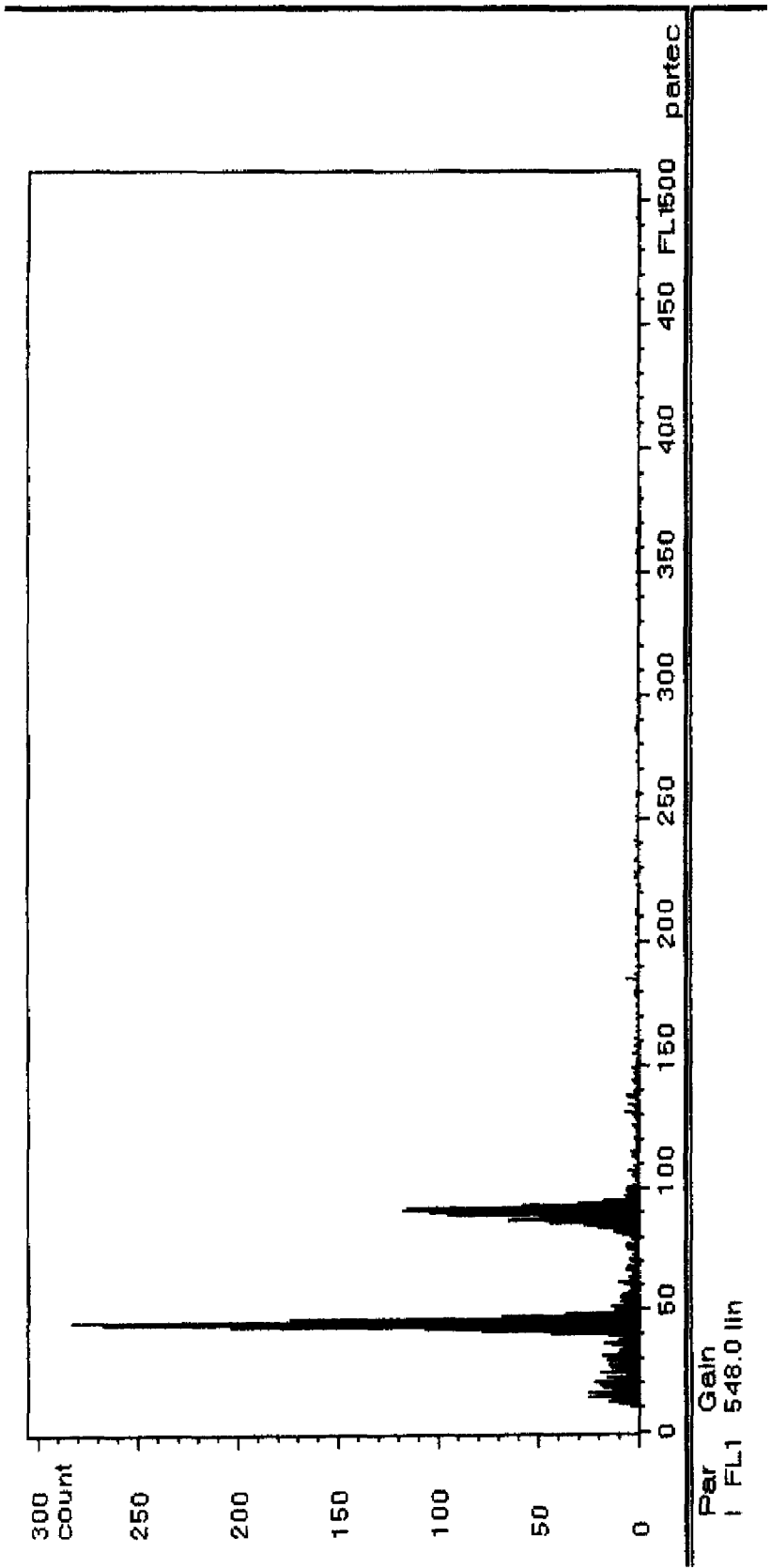
Figure 4C:
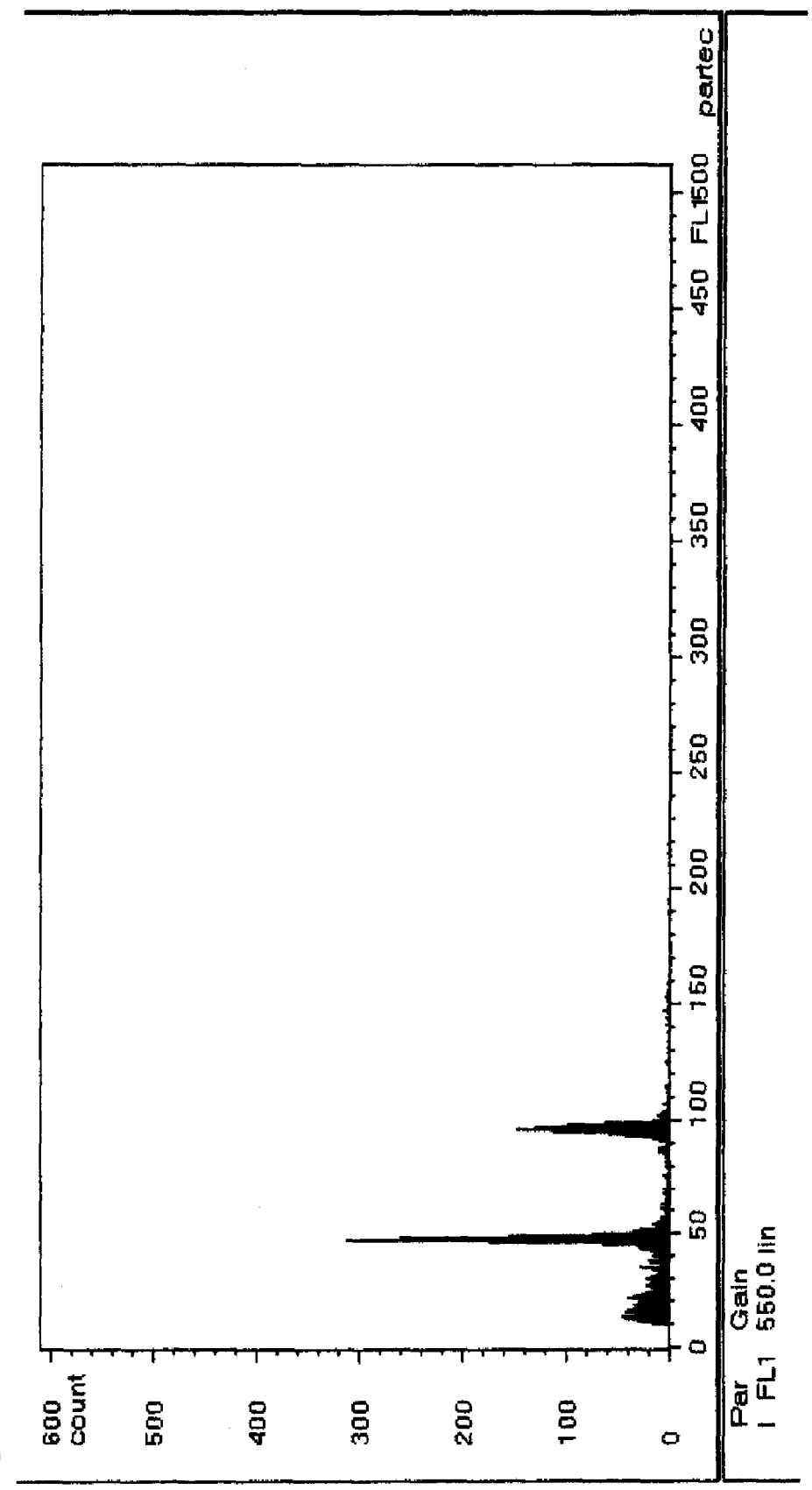
Figure 4D:
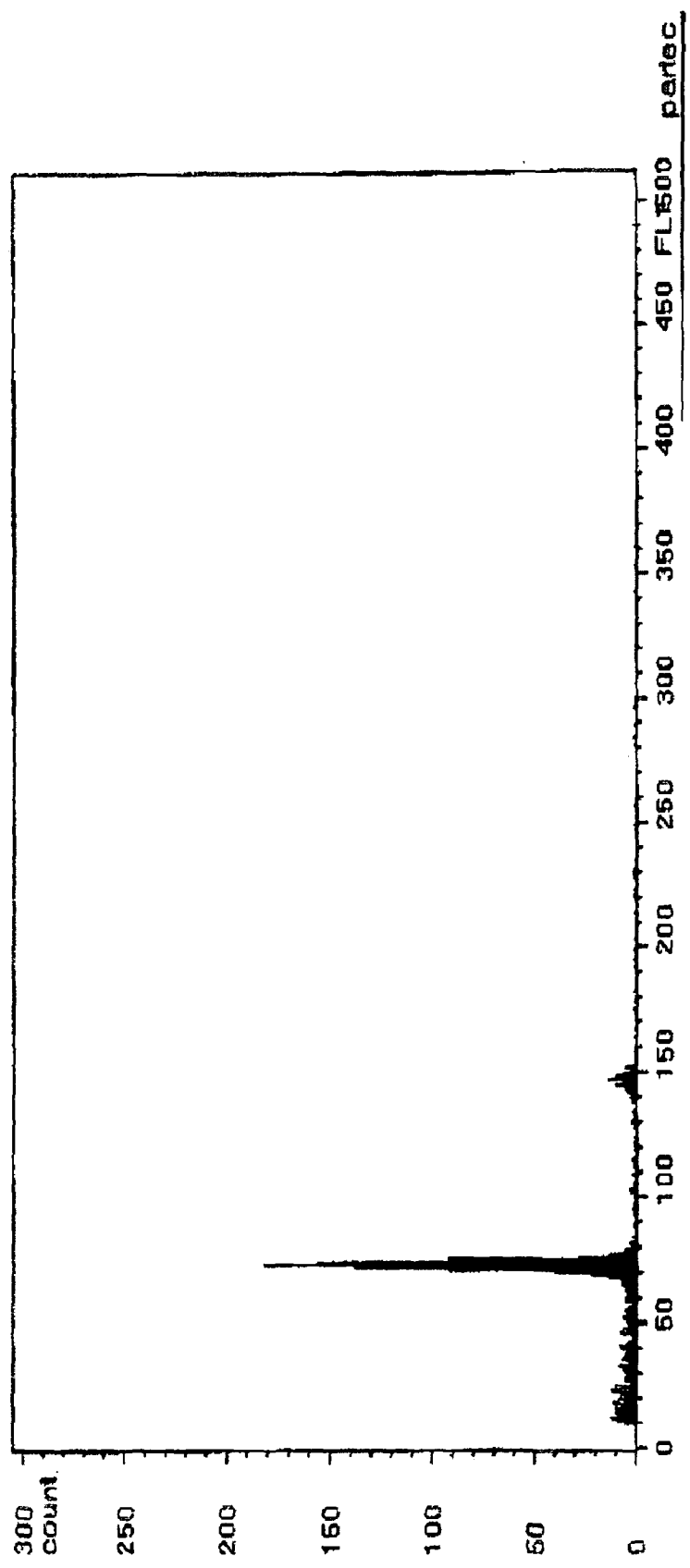

The surviving back-crossed progeny ($BC_1$) were all found to be triploid on the basis of DNA analysis by flow cytometry (see FIG. 4D compared to A,B and C), with a chromosome complement consistent with one set of cauliflower chromosomes (n=9) and 2 sets of *E. sativa* chromosomes (n=11) giving a total of 31 chromosomes.

The phenotypes of RQ1438/05-1 and -2 plants were very similar to that of E. sativa, but their vegetative growth was more vigorous (see FIG. 2 and FIG. 3), and their conversion to the sexual stage was also very severely delayed compared to E. sativa. RQ1438/05-1 was the first of the 3 plants to flower, and expressed a male-sterile phenotype, while otherwise having normal flower morphology. DNA marker analysis revealed that all 3 plants contained the "orf138" marker, showing that the "Ogura" CMS is present (See example 13+FIG. 5).

E. Back-Crossed Lines Derived from RQ14318/05 Plants Comprising *E. sativa* and CMS Traits RQ1438/05-1, of the $BC_1$ generation, was pollinated extensively with cv. "Myway" and 3 month after the first pollination a total of 33 $BC_2$ seeds were harvested, consistent with a low fertility.

Figure 8:
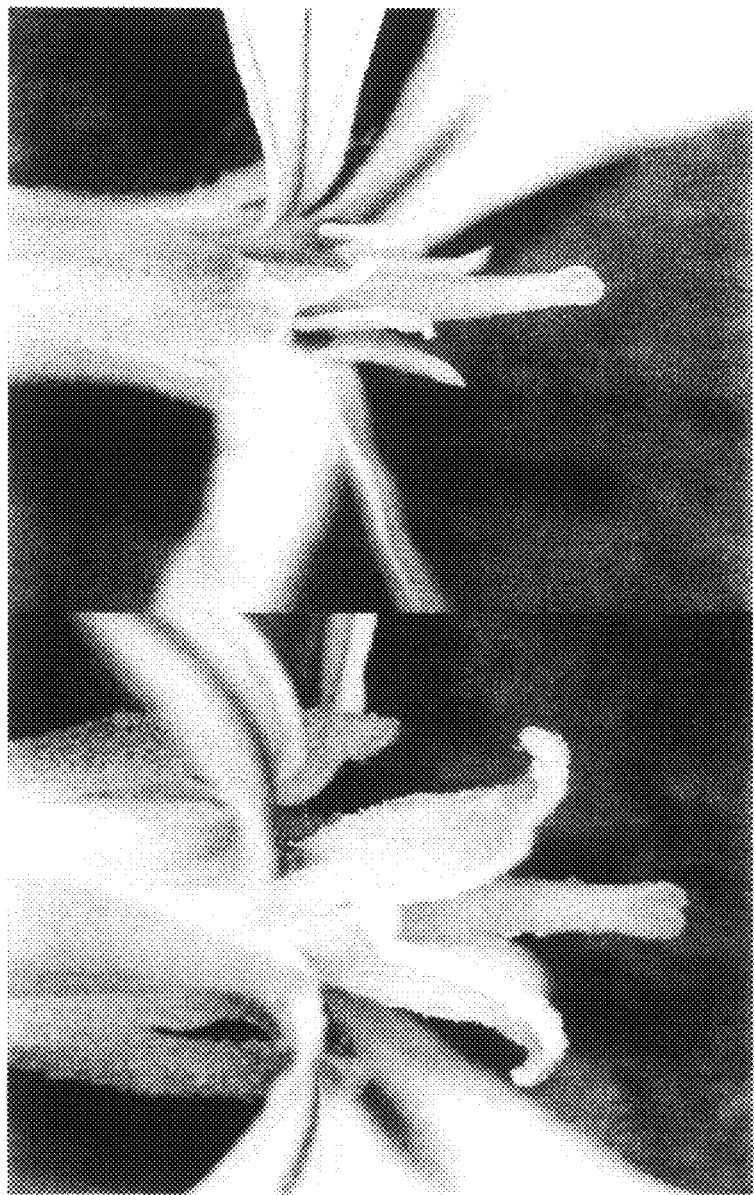
FIG. 8: Left: Normal flower of E. Sativa. Right: CMS-*E. sativa* flower (Line 5000/06). Anthers are shrunken and thin, i.e. not carrying pollen.

The 5 first mature $BC_2$ seeds (Line no. RQ 5000/06) were germinated and 5 individual $BC_2$ plants were obtained, all of which were male sterile. Of these plants, number 1 to 4 clearly resembled the *E. sativa* morphology, whereas number 5 was more vigorous. Apart from having dysfunctional anthers, the flowers of the $BC_2$ plants were now morphologically similar to *E. sativa* var. "Myway" (FIG. 8).

Figure 4E:
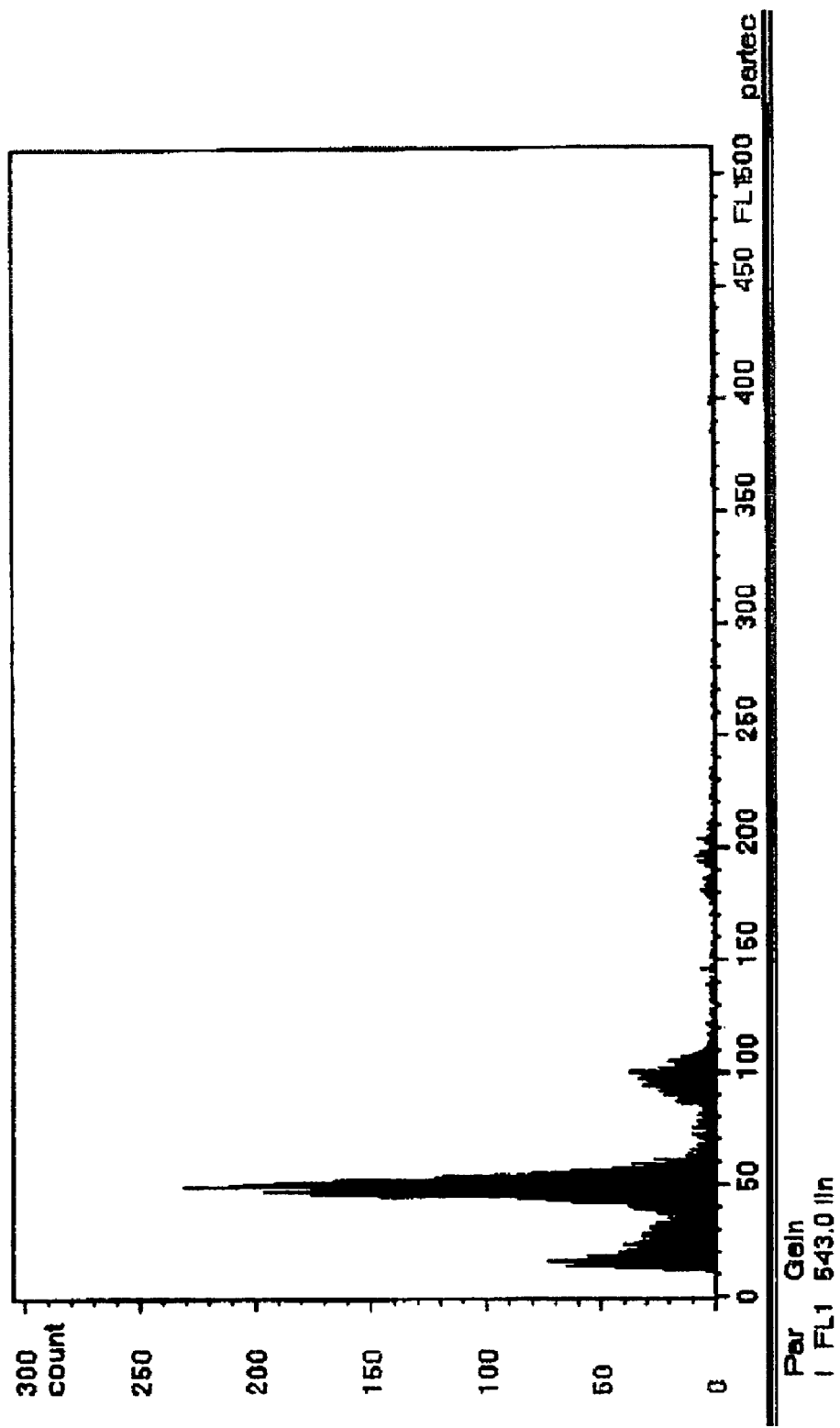
Figure 4F:
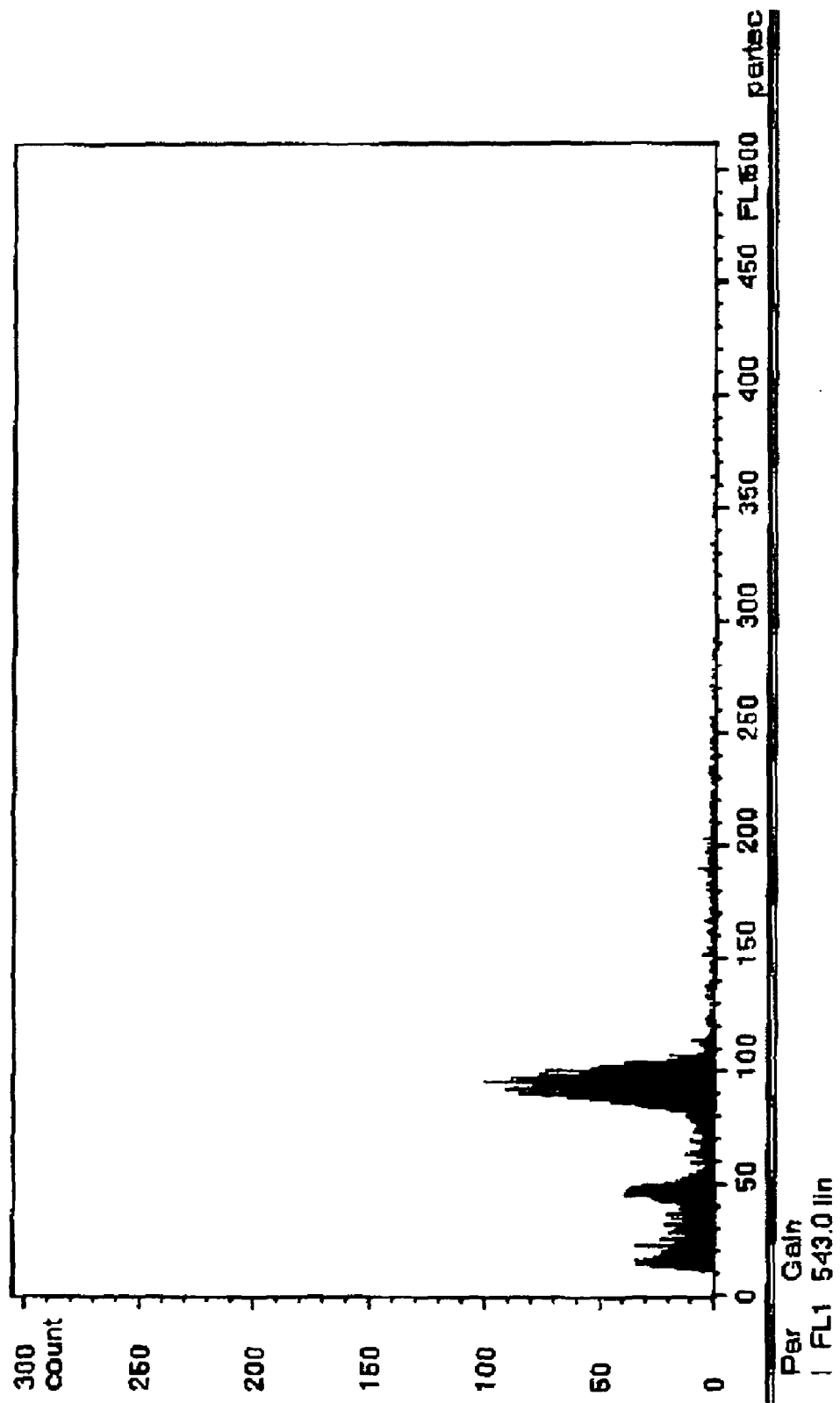

A flow cytometry analysis suggested that the plants 1, 2, 3 and 4 had reverted to diploid chromosome complement, and that plant number 5 was amphitetraploid carrying 3 sets of *E. sativa* and 1 set of B. oleracea chromosomes 3n=33+n=8=41 chromosomes. (FIGS. 4E-F). DNA marker analysis revealed that all 5 plants of RQ 5000/06 contained the "orf138" marker, showing that the "Ogura" CMS is present (Example 13+FIG. 5).

F. Diploid CMS *E. sativa* Derived from Back-Crossing of RQ1438/05 Plants

The four 4 $BC_2$ plants, identified as diploid E. sativa, yielded an average of 24.9 seeds/silique, which compares favourably with the male fertile E. sativa used as RP (Recurrent Parent), that yields an average of 17.3 seeds/silique. The amount of seed produced was normal for *E. sativa* in relation to the time of the year and the number of pollinations made, and on this basis it was concluded that female fertility was fully restored in the $BC_3$ plants. From these $BC_3$ seeds a deposit was made at NCIMB with Accession No. 41429. The $BC_3$ plants generated from RQ 5000/06 are indistinguishable from the recurrent parent *E. sativa* (cv. "Myway") at the harvest size normally used for commercial leaf production (See FIG. 9).

In order to determine the amount of *B. oleracea* DNA still present in the $BC_3$ plants generated from RQ 5000/06, a DNA marker analysis with 72 SSR markers covering the whole C-genome of *B. napus* was performed. The analysis (example 14) revealed that the $BC_3$ plants had very high homology to E. sativa, and that all of the *B. oleracea* chromosomes had been eliminated in the back-crossing process.

EXAMPLE 2

CMS *E. sativa* Generated by Protoplast Fusion

A. Seed Sterilization and Germination

Seeds of *B. oleracea* or *B. napus* with CMS are dipped for approximately 10 seconds in 70% alcohol and sterilized in a 1.5% sodium hypochlorite solution for two times for 10 minutes at 20° C. The sterilised seeds are then extensively rinsed with sterile distilled water. The seeds are then placed on the MS nutrient medium (see table 1) with 3% sucrose and without hormones. To obtain green sterile plants, the seeds are grown in glass jars in the light (8000 lux), for a 16 hour photoperiod with temperatures of 25° C. day and 20° C. night. Sterile shoots are subcultured under the same conditions in plastic containers. To obtain white tissue for protoplast isolation, e.g. hypocotyls, the seeds are grown in petri dishes in the dark at 25° C.

B. Isolation of Protoplasts

Leaves of four-week old shoots of plant material according to example 3 are cut into small pieces and incubated in an enzyme solution (table 4 A) for 16 hours at 25° C. on a gyratory shaker at 40 rpm. The suspension is filtered through a nylon mesh (40 μm) and washed with CPW 16S solution (table 4D) by centrifugation at 817 rpm for 5 minutes. This results in flotation of the intact protoplasts. The protoplasts are collected and rinsed twice with W5 solution (table 4B) by centrifugation at 708 rpm for 5 minutes. The protoplasts are diluted to a density of $1 \times 10^5$ protoplasts per ml W5 solution before being used for fusion experiments.

TABLE 4

| A. ENZYME SOLUTION (1 L) |
|---|
| 90 g mannitol |
| 0.0272 g $KH_2PO_4$ |
| 0.1 g $KNO_3$ |
| 0.246 g $MgSO_4 \cdot 7H_2O$ |
| 0.0008 g KI |
| 0.00025 g $CuSO_4 \cdot 5H_2O$ |
| 1.4 g $CaCl_2\ 2H_2O$ |
| 1.1 g MES |
| 6 g Cellulose R10 |
| 1 g pH 5.8 Macarozyme |
| B. WASHING SOLUTION (W5) (1 L) |
| 18.4 g $CaCl_2 \cdot 2H_2O$ |
| 4.91 g NaCl |
| 0.372 g KCl |
| 0.901 g glucose |
| pH = 5.8 |

TABLE 4-continued

C. WASHING SOLUTION (W5') (1 L)

18.4 g CaCl$_2$•2H$_2$O
4.91 g NaCl
0.372 g KCl
0.901 g glucose
9.76 g MES
pH = 5.8

D. CPW 16 S (1 L), 160 g sucrose
0.0272 g KH$_2$PO$_4$
0.1 g KNO$_3$
1.45 g CaCl$_2$•2H$_2$O
0.246 g MgSO$_4$•2H$_2$O
0.0008 g KI
0.025 mg CuSO$_4$•5H$_2$O,
pH = 5.5-5.8

E. PEG fusion solution (PFS), 18.8% PEG (MW 4000)
0.06 M CaCl$_2$•2H$_2$O
0.1 M mannitol,
0.025 M glucine,
10% (v/v) DMSO

F. SPA SOLUTION (1 L)

20 g SeaPlaque agarose, 100 g Sucrose

C. Preparation of Fluorescent-Stained Protoplasts

Six- to eight-day old hypocotyls of the plant material prepared according to example 2A are isolated according to the process of example 2B, except that 3 µg/ml of fluoresceinediacetate is added to the enzyme solution used during the enzyme treatment step. Stained protoplasts suitable for hand selection and for determination of fusion frequency are thus obtained.

D. Irradiation of Protoplasts

Freshly isolated protoplasts prepared according to example 2B are plated in a 6 cm petri dish in 2 to 3 ml W5 solution (table 4B). The protoplasts are irradiated using an X-ray source (Baltograph CE100), at a dose of 3500 Gy during 20 minutes. After irradiation, the inactivated protoplasts are washed with W5 solution by centrifugation at 708 rpm for 5 minutes. The protoplasts are diluted to a density of $1 \times 10^5$ protoplasts per ml W5 solution before being used for fusion experiments.

E. Fusion Procedure

Protoplasts according to example 2B, C and D, are mixed 1:3 in a final concentration of $1 \times 10^5$ protoplasts per ml W5 solution. Three droplets of 100 µl of the suspended protoplasts are placed in an uncoated 6 cm petri dish and the protoplasts are allowed to settle for 5 to 10 minutes. Three hundred µl of PFS solution is added in the center of the three droplets to induce agglutination for 15 minutes. Thereafter, 300 µl of W5 solution is added to the mixture, and again after 10 minutes, and again after a further 5 minutes. The W5 medium is replaced by two times concentrated 8P solution (table 1) and the protoplasts are cultivated for one to three days at 25° C. in the dark.

F. Selection and Growth of Fusion Products

The entire fusion mixture according to example 2E is cultured for one to three days in the dark at 25° C. The cells are collected by centrifugation at 548 rpm for 5 minutes and diluted in two times concentrated 8P medium to a density of $1 \times 10^5$ protoplasts per ml. An equal volume of 37° C. SPA medium (table 4F) is added and the cells are plated in 5 droplets of 100 µl in a coated petri dish C). Also 5 droplets of 100 µl with feeder cells (cell suspension that improve regeneration) are added. After two weeks, the droplets with feeder cells are removed (By using an pipette) and 2 ml MAC medium (table 1) per petri dish is added. After two weeks the droplets are dispersed on solid Br medium (table 1). After two to three weeks the individual colonies are transferred to a petri dish with solid K3 medium (table 1). The microcalli are cultured in low light intensity (2500 lux) at 25° C. with a photoperiod of 18 hours.

Fused cells, which can be recognized visually, for example by the presence of double fluorescence, are picked up with a micromanipulator. The hybrid cells are cultured in 100 µl agarose droplets (1% SeaPlaque) at a density of 2000 to 50,000 protoplasts per milliliter. The droplets are placed in a liquid nurse culture system (Costar-Transwell col) with feeder cells and incubated at 25° C. in the dark. The droplets are dispersed on solid Br medium (table 1) after two weeks. Small calli are transferred to solid K3 medium (table 1) and incubated at 25° C. in low light intensity (2500 lux) with a photoperiod of 16 hours.

G. Plant Regeneration

The calli according to examples 10 and 11, having developed to a size of 2 to 5 mm in diameter, are transferred to fresh K3 medium (table 1) at normal light intensity (8000 lux) at 25° C. with a photoperiod of 16 hours. Small shoots are transferred to B5 medium (table 1) with 1% sucrose without hormones and rooted on the same medium.

EXAMPLE 3

CMS Identification by DNA Markers

A DNA marker was used to detect the presence of "Ogura" CMS in plant material. Detection of the marker was based on a Polymerase Chain Reaction (PCR) procedure employing the primer combination oligo37 and oligo38 (table 5). This primer combination yields a 512 bp PCR fragment when the "Ogura" CMS-marker "orf138" is present.

TABLE 5

| | |
|---|---|
| Oligo 37 (upper primer): | 5'GCA TCA CTC TCC CTG TCG TTA TCG3' |
| Oligo 38 (lower primer): | 5'ATT ATT TTC TCG GTC CAT TTT CCA3' |
| Cob gene (upper primer): | TCT TCT CTC GGG GTC ATC CT |
| Cob gene (lower primer): | CCC CCT TCA ACA TCT CTC AT |

The PCR was performed on total DNA extracted from 16 samples consisting of cauliflower with and without "Ogura" CMS, normal male fertile cultivars of *E. sativa* and F1 and BC$_1$ crosses between CMS-*B. oleracea* and E. sativa. As an internal positive control a 630 bp marker ("cob gene") was used.

All analysed plant samples were first ground in liquid nitrogen. DNA was then extracted from 250 mg plant material from each sample by means of a CTAB based DNA extraction protocol (Eurofins, Chen D. H. & Ronald, P. C., 1999). Average DNA yield was 5 ng/µL. Standard PCR conditions were used with an annealing temperature of 53° C. The products of the PCR performed on the extracted DNA from each plant sample employing the two primer pairs (oligos 37/38 and cob gene primers) were analyzed on a 1.5% agarose gel stained with ethidium bromide, as shown in FIG. 5.

Figure 5A:
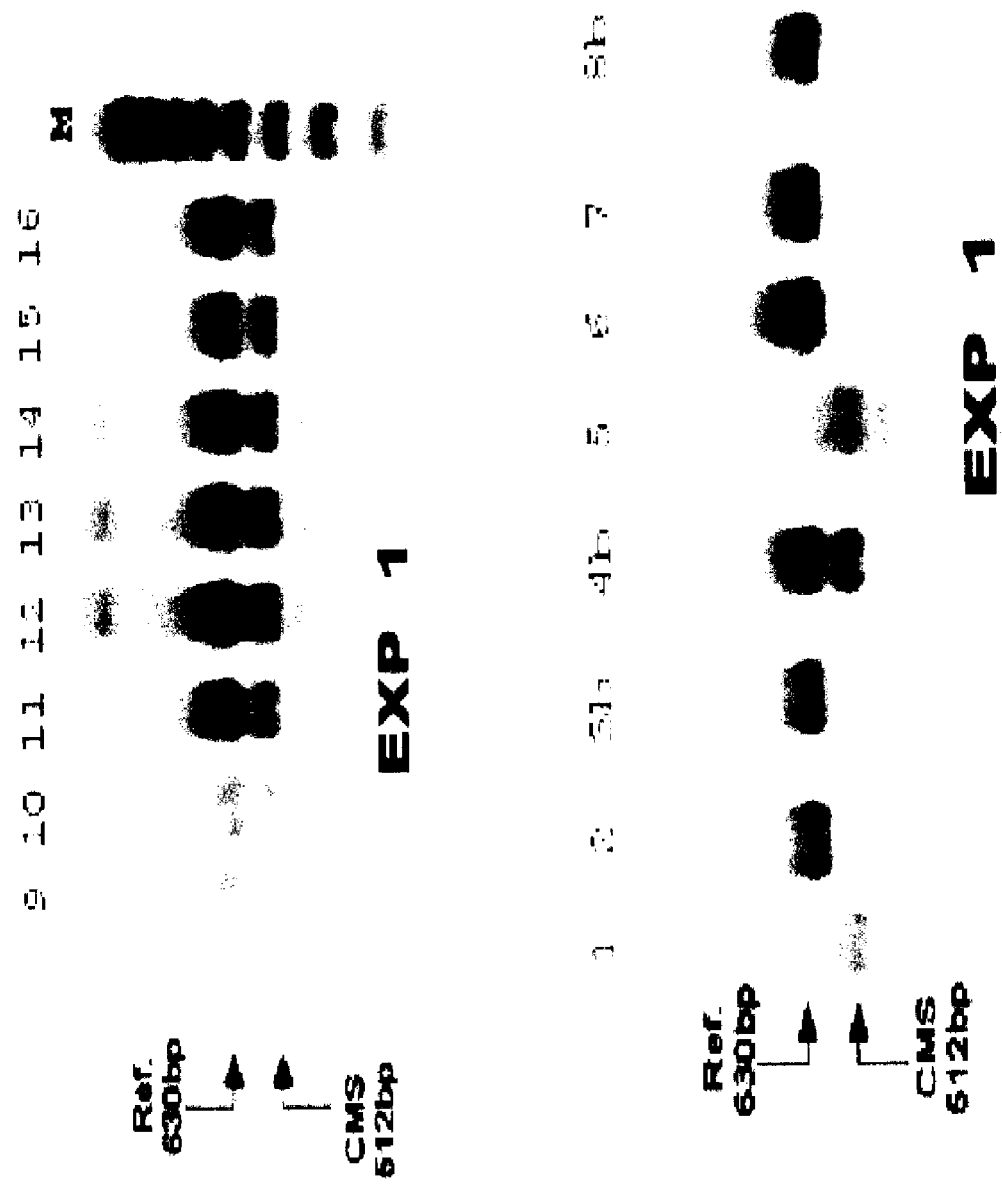

A DNA fragment of 512 bp was positively detected in the three cauliflower lines known to carry "Ogura" CMS (FIG. 5A, lanes 1, 4b, 5), while the 512 bp fragment was absent from 2 non-"Ogura" cauliflower lines (FIG. 5, lanes 2, 3b) and the 3 *E. sativa* lines (FIG. 5A, lanes 6, 7, 8b). The 8 DNA extracts from samples of different generation crosses between Cauliflower F1 hybrid cv. "Cheddar" and *E. sativa* (FIG. 5A, lanes 9-16) were all positive for the 512 bp fragment, indicating the presence of the orf138-gene in these interspecific hybrids.

Figure 5B:
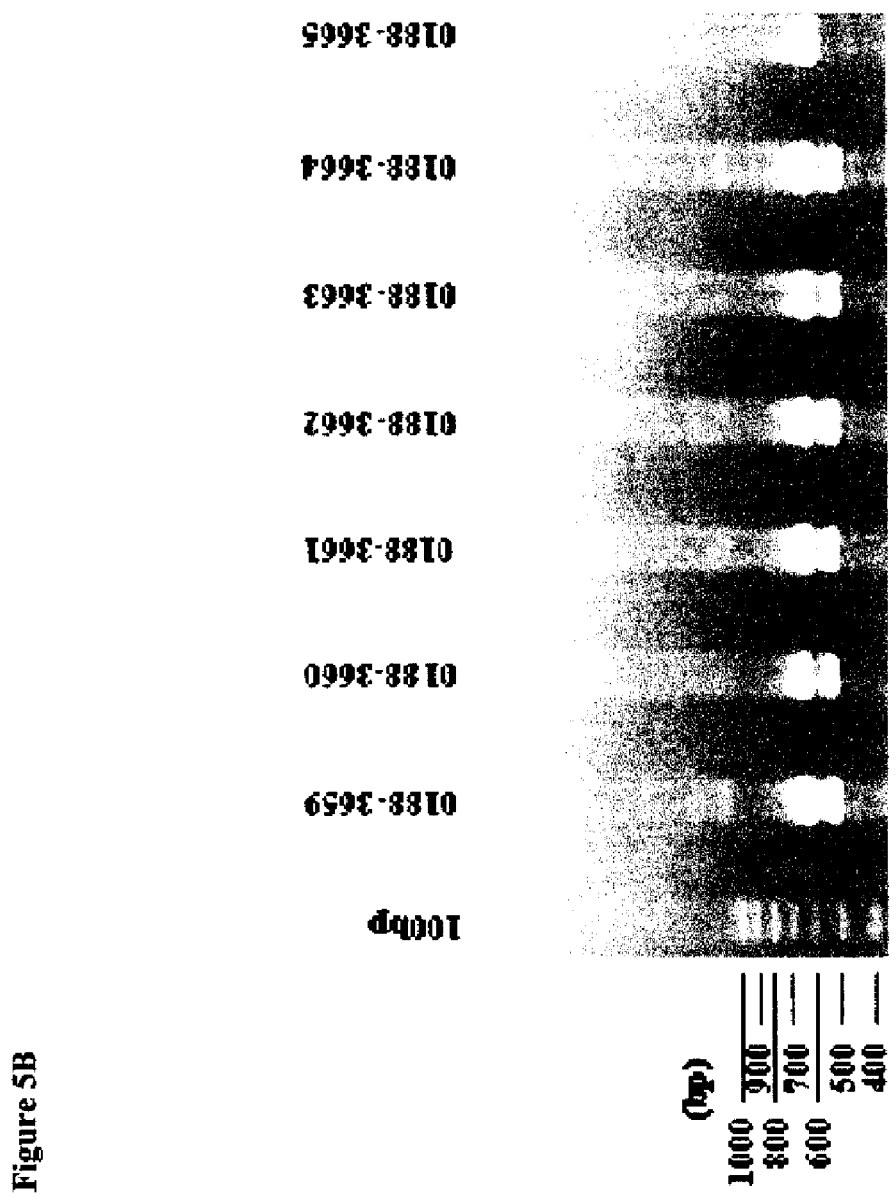

The 5 $BC_2$ plants of line RQ 5000/06 also tested positive for the 512 bp fragment, indicating the presence of the orf138 CMS marker in line RQ 5000/06 (see FIG. 5B).

EXAMPLE 4

Homology Studies by SSR Markers

Genomic DNA was extracted from five $BC_3$ plants generated from Line RQ 5000/06, and analysed with a set of 72 markers.

The markers used met the following criteria:
all markers map on the C-genome of the *B. napus* genetic map
8 markers cover each of the 9 linkage groups (chromosomes) of *B. oleracea* (the CMS donor, with C-genome).
the markers cover the C-genome of *B. napus* as evenly as possible The DNA fragment analysis was performed as a multi loading assay analyzing two or three markers, each labelled with a different ABI-dye, simultaneously. The test was designed to reveal the degree of homology between the $BC_3$ plants and the RP (*E. sativa* cv. "Myway").

47 of the markers were not amplified from DNA of *E. sativa* recurrent parent (RP), whereas only 2 of the markers were not amplified from DNA of the *B. oleracea* CMS donor plant. All of the markers were amplified from DNA of the *B. napus* containing the C-genome, which was included as a positive control. In total 4 of the markers were non informative (including the 2 that did not amplify in B. oleracea) because they showed an exact match between the *B. oleracea* CMS donor and the *E. sativa* RP. Therefore, they were discarded. A positive match is counted as an exact match between the amplification products of two samples. If a marker was not amplified in either the RP (*E. sativa*) or the $BC_3$ plants, this was also scored as a positive match.

TABLE 6

Percentage of exact positive matches between marker amplification products of the $BC_3$ plants derived from line RQ 5000/06, the *B. oleracea* CMS donor and the *E. sativa* RP.

| | % match to B. oleracea* | % match to E. sativa* |
|---|---|---|
| B. napus | 3 | 0 |
| B. oleracea | 100 | 0 |
| Plant 20 ($BC_3$) from RQ 5000/06 | 0 | 75 |
| Plant 21 ($BC_3$) from RQ 5000/06 | 0 | 75 |
| Plant 22 ($BC_3$) from RQ 5000/06 | 0 | 75 |
| Plant 23 ($BC_3$) from RQ 5000/06 | 0 | 75 |
| Plant 24 ($BC_3$) from RQ 5000/06 | 0 | 82 |

*The match percentage indicates the homology between the $BC_3$ plants, the CMS donor and the RP.

The match percentage indicates the homology between the $BC_3$ plants, the CMS donor and the RP. From table 6, it is seen that the $BC_3$ plants show a very high homology to E. sativa. The reason that the match is not 100% between the BC plants and the RP is that the RP is an open-pollinated variety and therefore it is not completely homozygotic. If all partial matches, i.e. a match in one of multiple amplified DNA fragments from a given marker, are included, the homology to *E. sativa* is between 85-90% in the $BC_3$ plants. None of the $BC_3$ plants show any homology to the CMS donor. It is therefore concluded that all the chromosomes of *B. oleracea* have been eliminated during the BC process.

REFERENCES

Cardi, T. & E. D. Earle, 1997. Production of new CMS *Brassica oleracea* by transfer of "Anand" cytoplasm from *B. rapa* through protoplast fusion, *Theoretical and Applied Genetics*, 94, 204-212

Cargill, Inc., PO Box 9300, Minneapolis, Minn., 55440-9300, USA, www.cargill.com Chen, D. H. & Ronald, P. C.; 1999. A rapid DNA minipreparation method suitable for AFLP and other PCR applications. *Plant Molecular Reporter*, 1999, p. 53-57.

Glimelius, 1984, *Physiologia Plantarum* 61:38

Hauptmann et al., 1983 "Carrot×Tobacco Somatic Cell Hybrids Selected by Amino Acid Analog Resistance Complementation", *6th International Protoplast Symposium, Basel*, Aug. 12-16, INRA, Agrocampus Rennes, BP 35327, F-35653 Le Rheu, France INRA, NCBI, acc. Z12626

Koop et al. 1989. *Electroporation and Electrofusion in Cell Biology*, edited: Neuman et al. pgs 355-365

L. Dæhnfeldt A/S, Faaborgvej 248B, 5250 Odense SV., Denmark

Seminis Vegetable Seeds, Oxnard, Calif., USA, www.seminis.com

Sigareva, M. A. & E. D. Earle, 1997, Direct transfer of a cold-tolerant "Ogura" male sterile cytoplasm into cabbage (*Brassica oleracea* ssp. *Capitata*) via protoplast fusion, Theoretical and Applied Genetics, 94, 213-220

Sundberg et al., 1986, *Plant Science*, 43:155

Sundberg, E. & Glimelius, K., 1991. Effects of parental ploidy level and genetic divergence on chromosome elimination and chloroplast segregation in somatic hybrids within Brassicaceae. *Theoretical and Applied Genetics*, vol. 83, no. 1, p. 81-82.

Syngenta Seeds B. V., Westeinde 62, P.O. Box 2, 1600 AA Enkhuizen, Netherlands. www.syngenta.com TraitGenetics GmbH, Am Schwabeplan 1b, D-06466 Gatersieben, Germany Tsunoda S., Hinata K. & Gómez-Campo C., 1980, *Brassica crops and wild allies, Japan Scientific Societies Press*, Tokyo Yadav, R. C., Yadav, N. R. & P. K. Sareen, 2002. Interspecific hybridization in different *Brassica* species: pollen tube studies. *National Journal of Plant Improvement*, vol. 4, p. 42-47.

The invention claimed is:

1. A method of producing a male sterile *Eruca sativa* plant, wherein said plant comprises a male sterile cytoplasm conferring male sterility upon said plant, comprising the steps of:
   a) crossing a cytoplasmic male sterile *Brassica oleracea* [or a cytoplasmic male sterile *Brassica napus*] plant comprising Ogura male sterile cytoplasm with an *Eruca sativa* plant,
   b) rescuing one or more embryos resulting from the cross of step a),
   c) regenerating a plant from one or more embryos of step b) and selecting one or more plant having *Eruca sativa* phenotype,
   d) doubling the chromosome number of the plant of step c), and
   e) back-crossing one or more plant resulting from step d) with an *Eruca sativa* plant and selecting for one or more plant with *Eruca sativa* phenotype.

2. The method according to claim 1, further comprising back-crossing one or more plant resulting from step e) with an *Eruca sativa* plant and selecting for one or more plant with *Eruca sativa* phenotype.

3. The method according to claim 1, wherein said selecting further includes testing for an orf138 DNA marker and wherein said selected plant comprises said marker.

4. The method according to claim 2 further comprising crossing said one or more selected plant to an *Eruca sativa* inbred to produce one or more hybrid plant.

* * * * *

SEQUENCE LISTING

<160> NUMBER OF SEQ ID NOS: 5

<210> SEQ ID NO 1
<211> LENGTH: 512
<212> TYPE: DNA
<213> ORGANISM: Eruca sativa -continued

<400> SEQUENCE: 1

| gcatcactct | ccctgtcgtt | atcgacctcg | caaggttttt | gaaacggccg | aaacgggaag | 60 |
|---|---|---|---|---|---|---|
| tgacaatacc | gcttttcttc | agcatataaa | tgcaatgatt | accttttcg | aaaaattgtc | 120 |
| cacttttgt | cataatctca | ctcctactga | atgtaaagtt | agtgtaataa | gtttctttct | 180 |
| tttagctttt | ttactaatgg | cccatatttg | gctaagctgg | ttttctaaca | accaacattg | 240 |
| tttacgaacc | atgagacatc | tagagaagtt | aaaaattcca | tatgaatttc | agtatgggtg | 300 |
| gctaggtgtc | aaaattacaa | taaaatcaaa | tgtacctaac | gatgaagtga | cgaaaaaagt | 360 |
| ctcacctatc | attaaagggg | aaatagaggg | gaaagaggaa | aaaaagagg | ggaaagggga | 420 |
| aatagagggg | aaagaggaaa | aaaaagaggg | gaaaggggaa | atagagggga | aagaggaaaa | 480 |
| aaaagaggtg | gaaaatggac | cgagaaaata | at |  |  | 512 |

<210> SEQ ID NO 2
<211> LENGTH: 24
<212> TYPE: DNA
<213> ORGANISM: Artificial Sequence
<220> FEATURE:
<223> OTHER INFORMATION: Chemically synthesized

<400> SEQUENCE: 2
gcatcactct ccctgtcgtt atcg                                          24

<210> SEQ ID NO 3
<211> LENGTH: 24
<212> TYPE: DNA
<213> ORGANISM: Artificial Sequence
<220> FEATURE:
<223> OTHER INFORMATION: Chemically synthesized

<400> SEQUENCE: 3
attattttct cggtccattt tcca                                          24

<210> SEQ ID NO 4
<211> LENGTH: 20
<212> TYPE: DNA
<213> ORGANISM: Artificial Sequence
<220> FEATURE:
<223> OTHER INFORMATION: Chemically synthesized

<400> SEQUENCE: 4
tcttctctcg gggtcatcct                                               20

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5 ccccccttcaa catctctcat                                              20